United States Patent [19]
Dolle, III et al.

[11] Patent Number: 5,972,719
[45] Date of Patent: Oct. 26, 1999

[54] COMBINATORIAL HYDROXY-AMINO ACID AMIDE LIBRARIES

[75] Inventors: Roland Ellwood Dolle, III, King of Prussia, Pa.; Tao Guo, Somerset, N.J.; Theodore Otto Johnson, Jr., Plainsboro, N.J.; Hitesh K. Patel, North Brunswick, N.J.; Shiwei Tao, Plainsboro, N.J.; Zhen Min He, Princeton, N.J.

[73] Assignee: Pharmacopeia, Inc., Princeton, N.J.

[21] Appl. No.: 08/743,960

[22] Filed: Nov. 5, 1996

[51] Int. Cl.$^6$ .................. G01N 33/53; G01N 33/543; G01N 33/551; C07C 23/00
[52] U.S. Cl. .................. 436/518; 436/523; 436/524; 435/7.1; 564/193
[58] Field of Search .............. 435/7.1; 436/501, 436/518; 564/193

[56] References Cited

U.S. PATENT DOCUMENTS

| 4,755,592 | 7/1988 | Raddatz et al. | 530/323 |
| 5,618,825 | 4/1997 | Baldwin et al. | 514/317 |

FOREIGN PATENT DOCUMENTS

| 0200406 | 10/1986 | European Pat. Off. . |

OTHER PUBLICATIONS

Gordon EM, et al, (1994) Applications of combinatorial technologies to drug discovery. 2. Combinatorial organic synthesis, library screening strategies, and future directions. J Med. Chem. 37:1385–4101, 1994.

*Primary Examiner*—Donald E. Adams
*Assistant Examiner*—Joseph W. Ricigliano
*Attorney, Agent, or Firm*—Heslin & Rothenberg, P.C.

[57] ABSTRACT

Combinatorial chemical libraries of Formula I

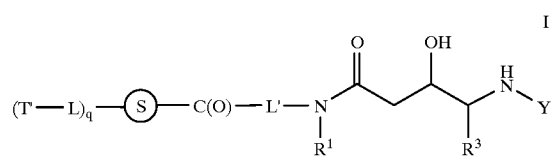

and methods for their preparation are disclosed. The libraries allow one to screen large numbers of compounds for a desired biological activity with relative ease. The libraries may be tagged or untagged. In preferred libraries, Y is the residue of an N-acylated amino acid, a substituted 4-aminoproline or a substituted piperazinealkanoic acid. The use of the libraries to discover biologically active compounds is also disclosed.

14 Claims, No Drawings

COMBINATORIAL HYDROXY-AMINO ACID AMIDE LIBRARIES

TECHNICAL FIELD

This invention relates generally to the synthesis of chemical compounds, and more particularly, to the synthesis of a combinatorial chemical library of hydroxy-amino acid amide compounds.

BACKGROUND OF THE INVENTION

Methods for the synthesis of large numbers of diverse compounds which can be screened for various possible physiological or other activities are of interest (Ellman, et. al., *Chem. Rev.*, 96, 555–600 (1996)). Synthesis techniques have been developed in which individual units are sequentially added to produce all or a substantial number of the possible compounds which can result from all the different choices possible at each sequential stage of the synthesis. For these techniques to be successful, it is necessary for the compounds to be amenable to methods by which one can determine the structure of the compounds so made. Examples of such techniques include, the technique of Brenner and Lerner [PNAS USA, 81, 5381–83 (1992) and WO 93/20242], according to which oligonucleotides are produced in parallel with, and are chemically linked as genetic tags, to oligopeptides as the compounds of interest. WO 93/06121 teaches methods for the particles-based synthesis of random oligomers wherein identification tags on the particles are used to facilitate identification of the oligomer sequence synthesized. Ohlmeyer, et al., *Proc. Natl. Acad. Sci. USA*, 90, 10922–10926 (December 1993), discloses a detachable tagging system.

SUMMARY OF THE INVENTION

The present invention relates to combinatorial libraries of compounds optionally encoded with tags, and to the use of these libraries in assays to discover biologically active compounds. The present invention further relates to two libraries of compounds containing amino- and carboxy-derivatized, 4-substitued-4-amino-3-hydroxybutyric acid (statine) residues and to the use of these two libraries to identify biologically active members of the libraries by screening bioassays.

I. Preferred Embodiments

The combinatorial chemical library of the present invention is represented by Formula I:

(T'—L—)$_q$(S)—C(O)—L'—Z   I wherein:
(S) is a solid support;
T'—L— is an identifier residue;
—L'—Z is a linker/compound residue;
q is 0–30; and
—Z is

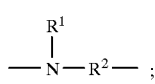

wherein:
$R^1$ is chosen from the group consisting of H, alkyl, cycloalkyl, and substituted alkyl; and
$R^2$ is —C(O)CH$_2$CH(OH)CH($R^3$)NH—
wherein:
$R^3$ is chosen from the group consisting of H, alkyl, aryl, arylalkyl and heteroarylalkyl; and Y is —C(O)$R^4$, —Aa—C(O)$R^4$, or —C(O)$R^5$;
wherein:
$R^4$ is chosen from the group consisting of alkyl, aryl, heteroaryl, substituted alkyl, cycloalkyl, substituted cycloalkyl, heterocycloalkyl and substituted heterocycloalkyl;
Aa is an amino acid;
$R^5$ is

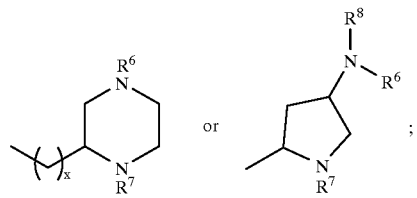

wherein:
x is 0 or 1;
$R^6$ and $R^7$ are each independently chosen from the group consisting of H, alkyl, substituted alkyl, alkylcarbonyl, substituted alkylcarbonyl and C(O)$R^4$; and
$R^8$ is alkyl or arylalkyl.

Preferred libraries of Formula I are those wherein T'—L— is of Formula II

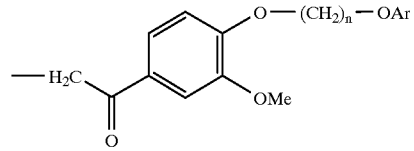

wherein:
n is 3–12;
Ar is halophenyl; and
q is 3–12.

More-preferred libraries of Formula I are those wherein T'—L— is of Formula II and n is 3–12 and Ar is a pentachlorophenyl or, n is 3–6 and Ar is 2,4,6-trichlorophenyl.

Other preferred libraries of Formula I are those wherein —L'— is of Formula (a)

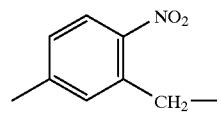

wherein the left-hand bond is the point of attachment to —C(O)— and the right-hand bond is the point of attachment to —Z.

Depending on the choice of —L'— (see Table 1), the compounds or ligands —Z of Formula I may be detached by photolytic, oxidative, acidic, basic, or other cleavage techniques. For example, when —L'— is of Formula (a), photolytic cleavage of compounds of Formula I may be represented by:

$$(T'\text{—}L)_q\text{—}(S)\text{—}C(O)\text{—}L'\text{—}Z \xrightarrow{\text{light}}$$

$$(T'\text{—}L)_q\text{—}(S)\text{—}C(O)\text{—}L'' + H\text{—}Z$$

wherein —L" is the residue from —L'— and H-Z is of Formula III:

$$HN(R^1)C(O)CH_2CH(OH)CH(R^3)NH\text{—}Y \qquad \text{III}$$

A preferred embodiment of the invention is a library of Formula I wherein:

$R^1$ is chosen from the 7 residues of the amines of Table 2-1;

$R^2$ is chosen from the 3 residues of the hydroxy amino acids of Table 2-2;

Y is —Aa—C(O)$R^4$;

Aa is chosen from the 31 residues of the amino acids of Table 2-3; and $R^4$ is chosen from the 20 residues of the carboxylic acids of Table 2–4.

Another preferred embodiment of the invention is a library of Formula I wherein:

$R^1$ is chosen from the 7 residues of the amines of Table 2-1;

$R^2$ is chosen from the 3 residues of the hydroxy amino acids of Table 2-2;

Y is —C(O)$R^5$;

$R^5$ is chosen from the 3 residues of the diamino acids in Table 3-1;

$R^6$ is chosen from the 15 residues of the aldehydes and carboxylic acids of Table 3-2; and $R^7$ is chosen from the 20 residues of the carboxylic acids of Table 3-3.

One aspect of the invention is the use of the combinatorial chemical library of Formula I in assays to discover biologically active compounds or ligands of Formula III. Thus, another aspect of the invention is a method of identifying a compound having a desired characteristic which comprises synthesizing a combinatorial chemical library of Formula I and testing the library compounds of Formula I, either attached to or detached from, the solid supports, in an assay which identifies compounds of Formula III having the desired characteristic. Thus, another aspect of the invention is a method of identifying a compound having a desired characteristic which comprises testing a library of compounds of Formula I, either attached to, or detached from, the solid support, in an assay which identifies compounds of Formula III having the desired characteristic. A further aspect of the invention is determining the structure of any compound so identified.

It is within the scope of the present invention that the chemical structures of compounds identified as having a desired characteristic can be determined by either decoding the tags (T, or T'—L— of Formula 1) or by deconvolution of the library. [See Smith et al., *BioMed. Chem. Lett.*, 4, 2821 (1994); Kurth et al., *J. Org. Chem.*, 59, 5862 (1994); Murphy et al., *J. Am. Chem. Soc.*, 117, 7029 (1995); Campell et al., *J. Am. Chem. Soc.*, 118, 5381 (1995); and Erb et al., *Proc. Natl. Acad. Sci. USA*, 91, 11422 (1994), the disclosures of which are incorporated herein by reference.].

When q is 0, the resultant untagged libraries are of Formula I':

$$(S)\text{—}C(O)\text{—}L'\text{—}Z \qquad \text{I'}$$

wherein each of the symbols is defined as in Formula I.

Another embodiment of the invention is a method of synthesizing a combinatorial chemical library of Formula Ia $$(S)\text{—}C(O)\text{—}L'\text{—}N(R^1)C(O)CH_2CH(OH)CH(R^3)NH\text{—}Y \qquad \text{Ia}$$

which comprises reacting a compound of Formula IV $$(S)\text{—}C(O)\text{—}L'\text{—}N(R^1)C(O)CH_2CH(OH)CH(R^3)NH_2 \qquad \text{IV}$$

with a carboxylic acid, dissolved in a suitable solvent such as dimethylformamide, at a concentration of 0.05M to 0.01M (high dilution), at 25° C., in the presence of DIEA and a suitable coupling reagent, such as HATU.

Another embodiment of the invention is a combinatorial chemical library of Formula IV, IVa, IVb, IVc, IVd or IVe.

$$(S)\text{—}C(O)\text{—}L'\text{—}N(R^1)C(O)CH_2CH(OH)CH(R^3)NH_2 \qquad \text{IV}$$

$$(S)\text{—}C(O)L'N(R^1)C(O)CH_2CH(OH)CH(R^3)NH\text{—}Aa\text{—}H \qquad \text{IVa}$$

IVb

IVc

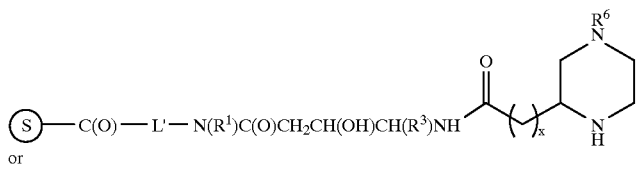

IVd

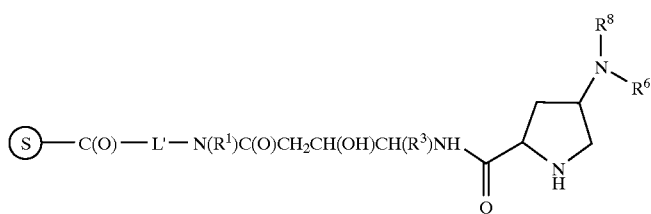

IVe wherein x is 0 or 1. This library of compounds is additionally useful as chemical intermediates in the preparation of sub-libraries within the combinatorial libraries of Formula I and I'.

Thus, another embodiment of the present invention is a combinatorial chemical library of Formula IVX

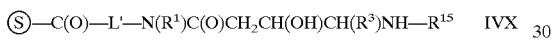　　IVX wherein

R$^1$ is

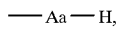

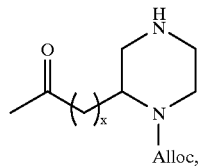

-continued

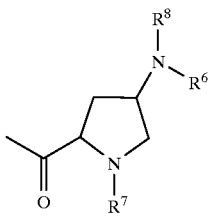

or

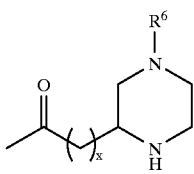

Another aspect of the invention is a method of synthesizing a combinatorial chemical library of Formula IVd or IVe which comprises reacting a compound of Formula V or VI

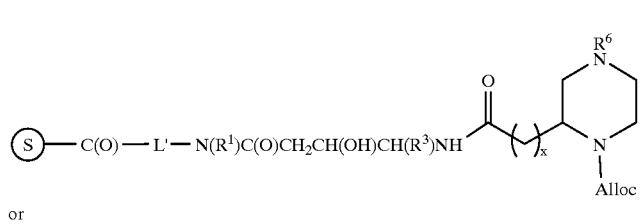

V or

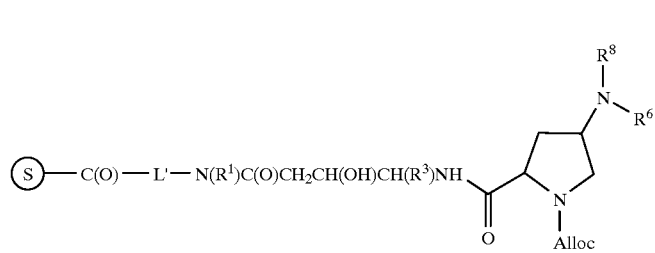

VI with a catalytic amount of palladium tetrakistriphenylphosphine or other palladium zero (Pd$^{10}$) catalysts in the presence of tributyltin hydride in acetic acid and methylene chloride at room temperature for about 1 hour.

Another embodiment of the invention is a method for synthesizing a carboxylic acid of Formula VII

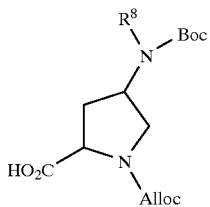

VII which comprises:

1) reacting a compound of Formula VIII

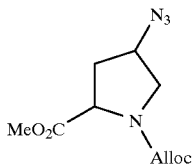

VIII with triphenylphosphine in toluene at room temperature for about 10 minutes and then evaporating the solvent and adding an aldehyde in the presence of sodium cyanoborohydride in methanol at 0° C. for 24 hours;

2) reacting the product of step 1 with Boc anhydride and a base in acetonitrile; and 3) hydrolyzing the product of step 2 with sodium or lithium hydroxide in tetrahydrofuran/water at reflux for 24 hours.

Another aspect of the invention is a method for preparation of a carboxylic acid ester of Formula VIII which comprises:

1) protecting the amine nitrogen of hydroxyproline using alloxychloroformate and a base;

2) esterifying the acid from step 1 with diazomethane to obtain a compound of Formula (c)

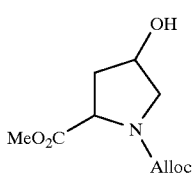

(c)

3) converting the alcohol from step 2 to a bromide with a brominating reagent; and 4) displacing the bromide of step 4 with sodium azide.

In another aspect, the invention relates to compounds of Formula (b)

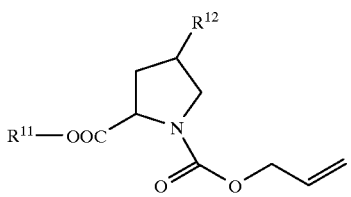

(b)

wherein

R$^{11}$ is H or methyl; and

R$^{12}$ is chosen from the group consisting of N$_3$, NH$_2$, NHR$_8$ and —N(Boc)R$^8$ wherein R$^8$ is alkyl or arylalkyl.

Another aspect of the invention is the use of divinylbenzene-cross-linked, polyethyleneglycol-grafted, polystyrene beads which are optionally finctionalized with amino groups, e.g., TentaGel™, SNH$_2$ and Rapp Polymere, as the solid supports for constructing a combinatorial chemical library of Formula I or I'.

DETAILED DESCRIPTION OF THE INVENTION

II. Abbreviations and Definitions

The following abbreviations and terms have the indicated meanings throughout:

| | |
|---|---|
| Alloc | allyloxy carbonyl |
| Bn | benzyl |
| BNB | 4-bromomethyl-3-nitrobenzoic acid |
| Boc | t-butyloxy carbonyl |
| Bu | butyl |
| DCM | Dichloromethane = methylene chloride = CH$_2$Cl$_2$ |
| DIC | diisopropylcarbodiimide |
| DIEA | diisopropylethyl amine |
| DMAP | 4-N,N-dimethylaminopyridine |
| DMF | N,N-dimethylformamide |
| DVB | 1,4-divinylbenzene |
| EDT | 1,2-ethanedithiol |
| FACS | fluorescence activated cell sorting |
| Fmoc | 9-fluorenylmethoxycarbonyl |
| HATU | O-(7-Azabenzotriazol-1-yl)1,1,3,3-tetramethyluronium-hexafluorophosphate |
| HOAc | acetic acid |
| HOBt | hydroxybenzotriazole |
| m- | meta |
| Me | methyl |
| Mtr | 4-methoxy-2,3,6-trimethylbenzenesulfonyl |
| Mtt | 4-methoxytrityl |
| N$_3$ | azido |
| NaBH$_3$CN | sodium cyanoborohydride |
| PEG | polyethylene glycol |
| Ph | phenyl |
| PhOH | phenol |
| PhSH | thiophenol |
| pmc | 2,2,5,7,8-pentethylchroman-6-sulfonyl |
| s- | secondary |
| t- | tertiary |
| TFA | trifluoroacetic acid |
| THF | tetrahydrofuran |
| TMS | trimethylsilyl |
| Trt | trityl = triphenylmethyl |

"Alkyl" is intended to include linear, branched, or cyclic hydrocarbon structures and combinations thereof "Lower alkyl" means alkyl groups of from 1 to 8 carbon atoms. Examples of lower alkyl groups include methyl, ethyl, propyl, isopropyl, butyl, s- and t-butyl, pentyl, hexyl, octyl, cyclopropylethyl, bornyl and the like. Preferred alkyl groups are those of C$_{20}$ or below.

"Cycloalkyl" is a subset of alkyl and includes cyclic hydrocarbon groups of from 3 to 8 carbon atoms. Examples of lower cycloalkyl groups include c-propyl, c-butyl, c-pentyl, norbornyl and the like.

"Alkenyl" includes $C_2$–$C_8$ unsaturated hydrocarbons of a linear, branched, or cyclic ($C_5$–$C_6$) configuration and combinations thereof. Examples of alkenyl groups include vinyl, allyl, isopropenyl, pentenyl, hexenyl, c-hexenyl, 1-propenyl, 2-butenyl, 2-methyl-2-butenyl, 2,4-hexadienyl and the like.

"Alkynyl" includes $C_2$–$C_8$ hydrocarbons of a linear or branched configuration and combinations thereof containing at least one carbon-carbon triple bond. Examples of alkynyl groups include ethyne, propyne, butyne, pentyne, 3-methyl-1-butyne, 3,3-dimethyl-1-butyne and the like.

"Alkoxy" refers to groups of from 1 to 8 carbon atoms of a straight, branched, cyclic configuration and combinations thereof. Examples include methoxy, ethoxy, propoxy, isopropoxy, cyclopropyloxy, cyclohexyloxy and the like.

"Acylamino" refers to acylamino groups of from 1 to 8 carbon atoms of a straight, branched or cyclic configuration and combinations thereof. Examples include acetylamino, butylamino, cyclohexylamino and the like.

"Halogen" includes F, Cl, Br, and I.

"Halophenyl" means phenyl substituted with 1–5 halogen atoms. Examples include pentachlorophenyl, pentafluorophenyl and 2,4,6-trichlorophenyl.

"Aryl" and "heteroaryl" mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S; each of which rings is optionally substituted with 1–3 lower alkyl, substituted alkyl, substituted alkynyl, =O, —$NO_2$, halogen, hydroxy, alkoxy, OCH(COOH)$_2$, cyano, —NRR, acylamino, phenyl, benzyl, phenoxy, benzyloxy, heteroaryl, or heteroaryloxy; each of said phenyl, benzyl, phenoxy, benzyloxy, heteroaryl, and heteroaryloxy is optionally substituted with 1–3 substituents selected from lower alkyl, alkenyl, alkynyl, halogen, hydroxy, alkoxy, cyano, phenyl, benzyl, benzyloxy, carboxamido, heteroaryl, heteroaryloxy, —$NO_2$ or —NRR (wherein R is independently H, lower alkyl or cycloalkyl, and —RR may be fused to form a cyclic ring with nitrogen);

The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Arylalkyl" means an alkyl residue attached to an aryl ring. Examples are benzyl, phenethyl and the like.

"Heteroarylalkyl" means an alkyl residue attached to a heteroaryl ring. Examples include, e.g., pyridinylmethyl, pyrimidinylethyl and the like.

"Heterocycloalkyl" means a cycloalkyl where one to two of the methylene (CH$_2$) groups is replaced by a heteroatom such as O, NR' (wherein R' is H or alkyl), S or the like; with the proviso that when two heteroatoms are present, they must be separated by at least two carbon atoms. Examples of heterocycloalkyl include tetrahydrofuranyl, piperidine, dioxanyl and the like.

"Alkylcarbonyl" means —C(O)R", wherein R" is alkyl.

"Substituted" alkyl, alkenyl, alkynyl, cycloalkyl, or heterocycloalkyl means alkyl, alkenyl, alkynyl, cycloalkyl, or heterocycloalkyl wherein up to three H atoms on each C atom therein are replaced with halogen, hydroxy, loweralkoxy, carboxy, carboalkoxy, carboxamido, cyano, carbonyl, —$NO_2$, —NRR; alkylthio, sulfoxide, sulfone, acylamino, amidino, phenyl, benzyl, heteroaryl, phenoxy, benzyloxy, heteroaryloxy, or substituted phenyl, benzyl, heteroaryl, phenoxy, benzyloxy, or heteroaryloxy.

"Aa" represents an amino acid and is intended to include the racemates and all optical isomers thereof The amino acid side chains of Aa include, e.g., methyl (alanine), hydroxymethyl (serine), phenylmethyl (phenylalanine), thiomethyl (cysteine), carboxyethyl (glutamic acid), etc. Primary and secondary amino acids are intended to include alanine, asparagine, N-β-trityl-asparagine, aspartic acid, aspartic acid-β-t-butyl ester, arginine, $N^g$-Mtr-arginine, cysteine, S-trityl-cysteine, glutamic acid, glutamic acid-γ-t-butyl ester, glutamine, N-γ-trityl-glutamine, glycine, histidine, $N^{im}$-trityl-histidine, isoleucine, leucine, lysine, $N^\epsilon$-Boc-lysine, methionine, phenylalanine, proline, serine, O-t-butyl-serine, threonine, tryptophan, $N^{in}$-Boc-tryptophan, tyrosine, valine, sarcosine, L-alanine, chloro-L-alanine, 2-aminoisobutyric acid, 2-(methylamino)isobutyric acid, D,L-3-aminoisobutyric acid, (R)-(–)-2 aminoisobutyric acid, (S)-(+)-2-aminoisobutyric acid, D-leucine, L-leucine, D-norvaline, L-norvaline, L-2-amino-4-pentenoic acid, D-isoleucine, L-isoleucine, D-norleucine, 2,3-diarninopropionic acid, L-norleucine, D,L-2-aminocaprylic acid, β-alanine, D,L-3-aminobutyric acid, 4-aminobutyric acid, 4-(methylamino)butyric acid, 5-aminovaleric acid, 5-aminocaproic acid, 7-aminoheptanoic acid, 8-aminocaprylic acid, 11-aminodecanoic acid, 12-aminododecanoic acid, carboxymethoxylamine, D-serine, D-homoserine, L-homoserine, D-allothreonine, L-allothreonine, D-threonine, L-threonine, D,L-4-amino-3-hydroxybutyric acid, D-,L-3-hydroxynorvaline, (3S,4S)-(–)-statine, 5-hydroxy-D,L-lysine, 1-amino-1-cyclopropanecarboxylic acid, 1-amino-1-cyclopentanecarboxylic acid, 1-amino-1-cyclohexanecarboxylic acid, 5-amino-1,3-cyclohexadiene-1-carboxylic acid, 2-amino-2-norbomanecarboxylic acid, (S)-(–)-2-azetidinecarboxylic acid, cis-4-hydroxy-D-proline, cis-4-hydroxy-L-proline, trans-4-hydroxy-L-proline, 3,4-dehydro-D,L-proline, 3,4-dehydro-L-proline, D-pipecolinic acid, L-pipecolinic acid, nipecotic acid, isonipecotic acid, mimosine, 2,3-diaminopropionic acid, D,L-2,4-diaminobutyric acid, (S)-(+)-diaminobutyric acid, D-ornithine, L-ornithine, 2-methylornithine, N-ε-methyl-L-lysine, N-methyl-D-aspartic acid, D,L-2-methylglutamic acid, D,L-2-aminoadipic acid, D-2-aminoadipic acid, L-2-aminoadipic acid, (+/–)-3-aminoadipic acid, D-cysteine, D-penicillamine, L-penicillamine, D,L-homocysteine, S-methyl-L-cysteine, L-methionine, D-ethionine, L-ethionine, S-carboxymethyl-L-cysteine, (S)-(+)-2-phenylglycine, (R)-(–)-2-phenylglycine, N-phenylglycine, N-(4-hydroxyphenyl)glycine, D-phenylalanine, (S)-(–) indoline-2-carboxylic acid, α-methyl,D,L-phenylalanine, β-methyl-D,L-phenylalanine, D-homophenylalanine, L-homophenylalanine, D,L-2-fluorophenylglycine, D,L-2-fluorophenylalanine, D,L-3-fluorophenylalanine, D,L-4-fluorophenylalanine, D,L-4-chlorophenylalanine, L-4-chlorophenylalanine, 4-bromo-D,L-phenylalanine, 4-iodo-D-phenylalanine, 3,3',5-triiodo-L-thyronine, (+)-3,3',5-triiodo-L-thyronine, D-thyronine, L-thyronine, D,L-m-tyrosine, D-4-hydroxyphenylglycine, D-tyrosine, L-tyrosine, O-methyl-L-tyrosine, 3-fluoro-D,L-tyrosine, 3-iodo-L-tyrosine, 3-nitro-L-tyrosine, 3,5-diiodo-L-tyrosine, D,L-dopa, L-dopa, 2,4,5-trihydroxyphenyl-D,L- alanine, 3-amino-L-tyrosine, 4-amino-D-phenylalanine, 4-amino-L-phenylalnine, 4-amino-D,L-phenylalanine, 4-nitro-L-phenylalanine, 4-nitro-D,L-phenylalanine, 3,5-dinitro-L-tyrosine, D,L-α-methyltyrosine, L-α-methyltyrosine, (−)-3-(3,4-dihydroxyphenyl)-2-methyl-L-alanine, D,L-threo-3-phenylserine, trans-4-(aminomethyl) cyclohexane carboxylic acid, 4-(aminomethyl)benzoic acid, D,L-3-aminobutyric acid, 3-aminocyclohexane carboxylic acid, cis-2-amino-1-cyclohexane carboxylic acid, γ-amino-β-(p-chlorophenyl)butyric acid (Baclofen), D,L-3-aminophenylpropionic acid, 3-amino-3-(4-chlorophenyl) propionic acid, 3-amino-3-(2-nitrophenyl)propionic acid, and 3-amino-4,4,4-trifluorobutyric acid.

The $R^2$ residues used in this invention were prepared by the method of Rich (Rich et al., *J. Org. Chem.*, 43, 3624 (1978)). Rich's method uses an amino acid aldehyde and an alpha-bromo carboxylic acid ester which are condensed via a Reformatsky reaction. Due to the broad scope of this reaction and the diverse selection of coupling partners which are known in the art, many $R^2$ residues, or statines, can be synthesized.

The linkers of the present invention may be any component capable of being selectively cleaved to release both T— and —Z from the solid support. See, e.g., Greene and Wuts, *Protective Groups in Organic Synthesis*, 2d ed., Wiley (1991). Specific linkers —L'— are depicted in Table 1 (note that —L—=—C(O)L'— or —CH$_2$—C(O)L'—), which also shows cleavage reagents. In designing a synthetic scheme, L and L' are chosen such that they are orthogonally reactive, i.e., they allow for removal of either T— or —Z (where T=T'OH) without removal of the other since simultaneous cleavage of both T— and —Z from the solid support is disadvantageous. In the structures as shown, the left-hand bond is the point of attachment to the solid support (via —C(O)— for L' and —C(O)— or —CH$_2$C(O)— for L) and the right-hand bond is the point of attachment to Z.

The tags of this invention, T (or T'—L— of Formula I), are chemical entities which possess several properties: they must be detachable from the solid supports, preferably by photolysis or oxidation; they must be individually differentiable, and preferably separable; they must be stable under the synthetic conditions; they must be capable of being detected at very low concentrations, e.g., $10^{-18}$ to $10^{-9}$ mole; they should be identifiable with readily-available equipment that does not require sophisticated technical capabilities to operate; and they should be relatively economical. The tags may be structurally related or unrelated, e.g., a homologous series, repetitive functional groups, related members of the Periodic Chart, different isotopes, combinations thereof, or the like. At the end of the combinatorial synthesis, attached to each solid support, there will typically be at least 0.01 femtomole, and more typically, 0.001–50 pmole, of each tag. The tags may be aliphatic, alicyclic, aromatic, heterocyclic, or combinations thereof. Distinguishing features may be the number of repetitive units, such as methylene groups in an alkyl moiety; alkyleneoxy groups in a polyalkyleneoxy moiety; halo groups in a polyhalo compound; α- and/or β-substituted ethylene groups where the substituents may be alkyl, alkoxy, carboxy, amino, halo, or the like; isotopes; etc.

The material upon which the combinatorial syntheses of the present invention are performed are referred to as solid supports, beads or resins. These terms are intended to include beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and soluble supports such as low molecular weight non-cross-linked polystyrene.

III. Optical Isomers—Diastereomers—Geometric Isomers

Some of the compounds described herein contain one or more asymmetric centers and may thus give rise to enantiomers, diastereomers, and other stereoisometric forms that may be defined, in terms of absolute stereochemistry, as (R)— or (S)— or, as (D)— or (L)— for amino acids. The present invention is meant to include all such possible diastereomers, as well as, their racemic and optically pure forms. Optically active (R)— and (S)—, or (D)— and (L)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

IV. Utility

The combinatorial chemical library of the present invention is useful as a screening tool for discovering new lead structures through evaluation of the compounds in the library across an array of biological assays, including the discovery of selective inhibition patterns across isozymes. Thus, the library is useful as a tool for drug discovery, i.e., it is a means to discover novel lead compounds by screening the library against a variety of biological targets, and also as a tool for the development of structure-activity relationships (SAR) in large families of related compounds.

Compounds of the combinatorial library may be evaluated while ligand —Z remains attached to the solid support, as in Formula I or I', or alternatively, ligand —Z may be detached prior to evaluation. With the compounds of Formula I or I', screening assays such as FACS sorting and cell lawn assays may be used. When ligand —Z is detached prior to evaluation, its relationship to its solid support is maintained, e.g., by location within the grid of a standard 96-well plate or by location of activity on a lawn of cells. Whether the compounds are tested attached to or detached from, the solid supports, the tags attached to the solid support associated with bioactivity may then be decoded to reveal the structural or synthetic history of the active compound (Ohlmeyer et al., *Proc. Natl. Acad. Sci. USA*, 90, 10922–10926 (December 1993) and Still et al., "Complex Combinatorial Chemical Libraries Encoded with Tags", WO 94/08051). Alternatively, the chemical structures of the compounds may be determined by deconvolution of the library.

The usefulness of such a library as a screening tool is demonstrated by Burbaum et al., *Proc. Natl. Acad. Sci. USA*, 92, 6027–6031 (June 1995), who describe the assaying of encoded combinatorial libraries for, e.g., carbonic anhydrase inhibition. Even when none of the compounds in a particular assay are found to be active for a given screen, such lack of activity often, however, provides useful SAR information.

V. Assays for Determining Biological Activity

Assays for evaluating the compounds of the present invention are well known in the art. Although one usually does not know a priori in which specific assays a particular library compound or group of library compounds will have activity, useful screening systems for use in assaying libraries of the format described herein, in order to identify activity with respect to a wide variety of enzymes and molecule targets have been developed and are illustrated by the following example.

1. Xanthine Oxidase Inhibition

The following materials are used:

3.9 μM hypoxanthine 0.3 mM 4-aminoantipyrene 2 mM 3,5-dichloro-2-hydroxybenzenesulfonate 50 mM sodium phosphate buffer, pH 7.5

5 U/mL horseradish peroxidase (Sigma P-6782, 5500 U/5 mg)

3 nM xanthine oxidase (buttermilk, Sigma X-4500, 16 U/mL) inhibitor

Reactions are carried out in 24 μL total volume in 96-well U-bottom polypropylene microtiter dishes (Costar) containing the test compounds 8 μL of sodium phosphate buffer, pH 7.5, is added to each well. A substrate mixture is prepared on ice by mixing 0.53 mL sodium phosphate buffer, 0.4 mL 4-aminoantipyrene (0.61 mg/mL), 0.4 mL 3,5-dichloro-2-hydroxybenzene-sulfonate (5.3 mg/mL), 4 μL horseradish peroxidase (Sigma P-6782, 5500 U/5 mg), and 128 μL hypoxanthine 920 μg/mL. 8 μL of the substrate mixture is then pipetted into each well. 8 μL xanthine oxidase (buttermilk, 9. 0 nM, Sigma X-4500, 16 U/mL) in sodium phosphate buffer, pH 7.5 (or buffer alone as a control) is added lost, directly into the reaction mixture. The plates are pulse-spun briefly in a tabletop centrifuge before reading absorbance. Absorbance is read using a dual kinetics program (490 minus 650 nm) for 15 min. at r.t. without automix, in a microplate reader (Molecular Devices Thermomax). Initial rates are calculated (Vmax program) and compared to those of reactions without inhibitor.

2. Plasmepsin II Inhibition

The assay mix contained 50 mM sodium acetate (pH 5.0), 1 mg/ml BSA, 0.01% Tween 20, 12.5% glycerol, 18% DMSO and 12 μM plasmepsin substrate. Twenty five μL of the assay mix was added to each well of a 96-well microtiter plate containing dried down bead eluate or empty control wells. The plates were then sonicated and mixed. 25 μL of 8 nM plasmepsin II, in 50 mM sodium acetate (pH 5.0), 1 mg/ml BSA, 0.01% Tween 20, and 12.5% glycerol, was added to the assay mix. The final concentrations were 4 nM plasmepsin II, 6 μM plasmepsin substrate, 9% DMSO, 50 mM sodium acetate (pH 5.0), 1 mg/ml BSA, 0.01% Tween 20, and 12.5% glycerol. The reaction was incubated for 10 minutes at 25° C. and then quenched by the addition of 25 μL of 1 M Tris (pH 8.5) and 50% DMSO to achieve a final concentration of 0.33 M Tris and 23% DMSO. The EDANS fluorescence was measured using a Tecan, SLT FluoStar fluorescence plate reader with an excitation filter of 350 nm and an emission filter 510 nm. The background was determined by 25 μL of 50 mM sodium acetate (pH 5.0), 1 mg/ml BSA, 0.01% Tween 20, and 12.5% glycerol without enzyme.

Other examples of assay methods for evaluating the compounds of the present invention are disclosed in the following references:

*ACE Inhibition*—Holmquist et al., "A Continuous Spectrophotometric Assay for Angiotensin Converting Enzyme", *Anal. Biochem.*, 95, 540–548 (1979).

*Thrombin Inhibition*—Lottenberg et al., "Assay of Coagulation Proteases Using Peptide Chromogenic and Fluorogenic Substrates", *Meth. in Enzymol.*, 80, 341–361, (1981).

*Carbonic Anhydrase Inhibition*—Maren and Couto, "The Nature of Anion Inhibition of Human Red Cell Carbonic Anhydrases", *Archiv. of Biochem. and Biophy.*, 196, No. 2, Sept., 501–510 (1979).

*Carbonic Anhydrase Inhibition*—Ponticelo et al., "Thienothiopyran-2-sulfonamides: A Novel Class of Water-Soluble Carbonic Anhydrase Inhibitors", J. Med. Chem., 30, 591–597 (1987).

VI. Methods of Synthesis

The compounds of the present invention may be prepared according to the following methods. During each step in the syntheses that follow, each solid support upon which a compound is being synthesized, is uniquely tagged to define the particular chemical event(s) occurring during that step. The tagging is accomplished using identifiers, such as those of Formula II, which record each of the sequential events to which the support is exposed during the synthesis. Tagging thus provides a reaction history for the compound produced on each support. The identifiers are used in combination with one another to form a binary or higher order encoding scheme permitting a relatively small number of identifiers to encode a relatively large number of reaction products. For example, when used in a binary code, N identifiers can encode up to $2^N$ different compounds and/or conditions. By associating each variable or combination of variables at each step of the synthesis with a combination of identifiers which uniquely defines the chosen variables, e.g., reactants, reagents, reaction conditions, or combinations of these, one can use identifiers to define the reaction history applied to each solid support.

In carrying out the syntheses, one begins with at least $10^4$, and desirably at least $10^7$, and generally not exceeding $10^{15}$, solid supports. Depending on the pre-determined number of $R^1$ choices for the first step, one divides the supports accordingly into as many containers. The appropriate reagents and reaction conditions are applied to each container and then the combination of identifiers that encodes for each $R^1$ choice is added and attached. Depending on the chemistries involved, the tagging may be done prior to, concomitantly with, or after the reactions which comprise each choice. As a control, sample supports may be picked at any stage and a portion of their tags bound to the sample supports. As needed, one may wash the beads free of any excess reagents or by-products before proceeding. At the end of each step, the supports are pooled, mixed to homogeneity, and again divided, this time into as many containers as pre-determined for the number of $R^2$ choices for the second step in the synthesis. This procedure of dividing, reacting, tagging, and remixing is repeated until the combinatorial synthesis is completed.

A. Scheme 1: Derivatizing resin with bis-Boc lysine.

A batch of amino-functionalized PEG-grafted polystyrene beads 3, e.g., TentaGel™ amine, may be modified with bis-Boc lysine 2 to increase the available reaction sites for ligand attachment. Bis-Boc lysine 2 is coupled to the amino-functionalized beads 3 by amide bond formation. Coupling is achieved by reacting a suspension of beads 3 in DCM and adding 2, HOBt and DIC. The suspension is shaken overnight, drained or filtered, and then washed in succession with DMF, MeOH and DCM, yielding derivatized resin 1 which is then dried overnight under vacuum.

The lysine-loaded derivatized resin 1 is divided into a pre-determined number of reaction vessels for identification through tagging . In this instance, since seven $R^1$ amine residues are used in the first combinatorial step, equal portions of resin 1 are placed into seven reaction vessels. Identifiers are then added to each vessel, prior to the addition of a photo-labile linker and $R^1$ residues.

Unique tagging of the resin supports 1 in each reaction vessel is achieved with the addition of combinations of additional identifiers, encoded in a binary scheme, as depicted in Table 2-1 for each of the seven $R^1$ choices. Identifiers (of Formula IX, herein below) are attached by adding a solution of up to two identifiers in DCM (in a 7.5–15% wt./wt. identifier to solid support ratio, depending on the signal strength of the identifier) to a batch of supports suspended in ethyl acetate or DCM and shaking the mixture for 0.5–1 hour. A dilute solution of rhodium trifluoroacetate dimer is added, the mixture is immediately shaken overnight, and then washed in DCM. The procedure is repeated as necessary to add additional identifiers. For the purposes of simplicity, identifiers are not shown in the schematics.

B. Scheme 2

The seven $R^1$ amine choices (see Table 2-1) are added to the reaction vessels, each containing its own uniquely tagged resin. The $R^1$ amines are attached to resin 1 through the photo-labile linker, 4-bromomethyl-3-nitrobenzoic acid (BNB). This attachment is accomplished in two steps.

Step 1. The Boc protecting group 2 on resin 1 is removed and the BNB is attached by the following method. A suspension of tagged resin 1 in 1:1 TFA/DCM is shaken for about 1 hour, then washed in succession with DCM, MeOH, 4:1 MeOH/Et$_3$N, MeOH, DMF and DCM. The resultant bis-amine resin 4 is suspended in DCM, and treated with a solution of BNB, HOBt and DIC in DCM. The suspension is shaken for about 3 hours, then drained and washed with DCM. The tagged BNB resin 6 is dried overnight under vacuum. This process is repeated for each of the seven reaction vessels.

Step 2. The seven batches of tagged BNB resin 6 from step 1 are reacted with a unique primary amine (Table 2-1) to generate compound 7. The coupling of the amine to resin 6 occurs through displacement of the linker bromide and formation of a new carbonnitrogen bond. As a quality control for the reaction in this combinatorial step, a small portion of each batch of coupled resin 7 may be removed and titrated with picric acid to determine the extent of amine loading.

C. Scheme 3

Amine resins 7 are pooled, mixed, and divided into a pre-determined number of reaction vessels. Unique tagging of the supports in each reaction vessel is achieved with combinations of additional identifiers, encoded in a binary scheme, shown in Table 2-2. The identifiers are attached by adding a solution of up to two identifiers in DCM (in a 7.5–15% wt./wt. identifier to solid support ratio, depending on the signal strength of the identifier) to a batch of supports suspended in ethyl acetate or DCM and shaking the mixture for 0.5–1 hour. A dilute solution of rhodium trifluoroacetate dimer is added and the mixture is immediately shaken overnight, then washed in DCM. The procedure is repeated as necessary to add additional identifiers.

The mixtures of amines 7 in each vessel are then treated with a hydroxy-amino acid reagent (statine) 8 which corresponds to one of the three $R^2$ choices in Table 2-2. Each hydroxy-amino acid 8 is coupled to amine resin 7 by amide bond formation to produce compounds 9, which are then pooled and mixed. Mixed compounds 9 are then divided into two portions; one portion is taken through the chemistry of Schemes 4 and 5 to produce a library of compounds as in Example 1, and the other portion is sequentially taken through Schemes 6, 7 and 8 to produce a library of compounds as in Example 2. Thus, two separate libraries are produced having synthons $R^1$ and $R^2$ in common.

D. Scheme 4 (With Scheme 5, yields a library of compounds as in Example 1)

In this chemistry, mixed and pooled resin compound 9 is divided into a pre-determined number of reaction vessels and then tagged, prior to removal of the Boc protecting group and the attachment of $R^3$ residues. Unique tagging of the supports in each reaction vessel is achieved with combinations of additional identifiers encoded in a binary scheme, as depicted in Table 2-3. The identifiers are attached by adding a solution of up to two identifiers in DCM (in a 7.5–15% wt./wt. identifier to solid support ratio, depending on the signal strength of the identifier) to a batch of supports suspended in either ethyl acetate or DCM and shaking the mixture for 0.5–1 hour. A dilute solution of rhodium trifluoroacetate dimer is added and the mixture is immediately shaken overnight, then washed in DCM. The procedure is repeated as necessary to add additional identifiers.

Tagged resin 9 is treated with TFA/DCM to remove the Boc protecting group, thus exposing the terminal amino group and forming compounds 10. Each reaction vessel is then treated with one amino acid reagent 11, corresponding to one of the thirty-one choices of Aa (see Table 2-3), for separate coupling of each amino acid to compound 10 by amide bond formation to produce compounds 12. The amino acids are introduced with the base-labile Fmoc on the alpha-nitrogen atom. In cases where it is necessary to protect the amino acid side chains, an acid-protecting group may be used (protected Aa side chains are depicted as Aa' in Schemes 4 and 5).

E. Scheme 5

Compounds 12 are pooled, mixed, and divided into a pre-determined number of reaction vessels. The mixture of compounds 12 is treated with piperidine/DMF to deprotect the amino group by removing the Fmoc protecting group, thus giving rise to compounds 13. which in turn, are treated with one carboxylic acid reagent, corresponding to one of the 20 choices of $R^4$ shown in Table 2–4, thus generating compounds 14. In a final reaction in this chemistry, compounds 14 are exposed to a cocktail of TFA, PhOH, PhSH, and EDT in water. This protocol removes any protecting groups which happen to be present on either the amino acid (Aa') side chains or the $R^4$ residues, and produces library compounds 15 (illustrated hereinafter by Example 1). The resultant resin batches may then be tagged as described above or retained separately as sub-libraries. Amides of Formula III may be cleaved from resin compounds 15 by exposing them to UV light (ca. 360 nm) for 15–180 minutes at 25–50 ° C. in a suitable solvent such as methanol.

F. Scheme 6 (With Schemes 7 and 8, yields a library of compounds as in Example 2)

In this chemistry, mixed and pooled resin compound 9 (from Scheme 3) is divided into a pre-determined number of reaction vessels and then tagged, prior to removal of the Boc protecting group and the attachment of $R^5$ residues. Unique tagging of the supports in each reaction vessel is achieved with combinations of additional identifiers encoded in a binary scheme, as depicted in Table 3-1. The identifiers are attached by adding a solution of up to two identifiers in DCM (in a 7.5–15% wt./wt. identifier to solid support ratio, depending on the signal strength of the identifier) to a batch of supports suspended in either ethyl acetate or DCM and shaking the mixture for 0.5–1 hour. A dilute solution of rhodium trifluoroacetate dimer is added and the mixture is immediately shaken overnight, then washed in DCM. The procedure is repeated as necessary to add additional identifiers.

The tagged resin compounds 9 in each reaction vessel are treated with TFA/DCM to remove the Boc protecting group, thus exposing the terminal amino group and forming compounds 10. Each reaction vessel is then treated with one diamino acid 17, corresponding to one of the three choices for $R^5$ in Table 3-1, for separate coupling of each diamino acid to compounds 10 by amide bond formation with HATU and DIEA, to produce compounds 18.

G. Scheme 7

Compounds 18 are pooled, mixed, divided into a predetermined number of reaction vessels and then tagged, prior to removal of the Boc protecting group on the $R^5$ ligand and attachment of $R^6$ residues. Unique tagging of the supports in each reaction vessel is achieved with combinations of additional identifiers encoded in a binary scheme, as depicted in Table 3-2. The identifiers are attached by adding a solution of up to two identifiers in DCM (in a 7.5–15% wt./wt. identifier to solid support ratio, depending on the signal strength of the identifier) to a batch of supports suspended in either ethyl acetate or DCM and shaking the mixture for 0.5–1 hour. A dilute solution of rhodium trifluoroacetate dimer is added and the mixture is immediately shaken overnight, then washed in DCM. The procedure is repeated as necessary to add additional identifiers.

The mixtures of compounds 18 are then treated with TFA/DCM to selectively remove the Boc protecting group on the diamino acid ligand $R^5$ to produce amines 19. Each vessel is then treated with one carboxylic acid reagent or one carboxaldehyde, corresponding to one of the fifteen choices for $R^6$ (see Table 3-2) for either separate coupling of each carboxylic acid to compound 19 by amide bond formation or separate reductive amination of each carboxaldehyde to compound 19 to produce resin 20.

H. Scheme 8

Compounds 20 are pooled, mixed, divided into a predetermined number of reaction vessels and then treated with palladium tetrakistriphenylphosphine, tributyltin hydride in acetic acid and DCM to selectively remove the Alloc protecting group on the diamino acid $R^5$, producing amine compounds 21. All but one reaction vessel is then treated with one carboxylic acid reagent, corresponding to one of the $R^7$ choices 2 through 20 in Table 3-3, for separate coupling of each carboxylic acid to compounds 21 by amide bond formation to produce library resin compounds 22 (illustrated by Example 2). The remaining reaction vessel, to which no carboxylic acid is coupled, produces compound 22 wherein $R^7$ is H. The resultant resin batches may be tagged as described above or retained separately as sub-libraries. Amides of Formula III may be cleaved from resin 22 through exposure of the resin to UV light (ca. 360 nm) for 15–180 minutes at 25–50° C. in a suitable solvent such as methanol.

I. Scheme 9

Diamino acid intermediate 23 (compound 3 in Table 3-1) is prepared from hydroxy proline 24 by first treating it with alloxychloroformate, in a solvent such as water, in the presence of a base, e.g., potassium carbonate to yield Alloc protected compound 25. Compound 25 is esterified with either acid in methanol or diazomethane in diethyl ether, producing ester 26, which is then converted to bromide compound 27 using a brominating reagent such as triphenylphosphine and carbon tetrabromide. The bromide substituent is in turn displaced with azide using either sodium or potassium azide in DMF. Resultant azide compound 28 is then reductively alkylated with acetaldehyde, by first treating compound 28 with triphenylphosphine to generate an imine which is in turn reduced to an N-ethyl amino group in compound 29. Any number of aldehydes can be used in this reduction step, thus introducing a variety of $R^8$ groups. Amine 29 is treated with Boc anhydride in acetonitrile to produce compound 30 which in turn is hydrolyzed to carboxylic acid compound 23 by the action of lithium hydroxide in water.

VII. Preparation of Identifiers

Eleven compounds of the general formula IX

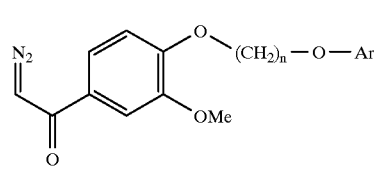

IX wherein n is 3–12 and Ar is pentachlorophenyl; or n is 6 and Ar is 2,4,6-trichlorophenyl, were prepared in accordance with Scheme 10 and the following illustrative example.

Step 1—1-hydroxy-9-(2,3,4,5,6-pentachlorophenoxy) nonane (1.634 g, 4.0 mmol), methyl vanillate (0.729 g, 4.0 mmol) and triphenylphosphine (1.258 g, 4.8 mmol) were dissolved in 20 mL dry toluene under argon. DEAD (0.76 mL, 0.836 g, 4.8 mmol) was added dropwise and the mixture was stirred at 25° C. for one hour. The solution was concentrated to half volume and purified by flash chromatography, eluting with DMC to yield 1.0 g (1.7 mmol, 43%) of the product as a white crystalline solid.

Step 2—The methyl ester product of step 1 (1.0 g, 1.7 mmol) was dissolved in 50 mL THF, 2 mL water was added, followed by LiOH (1.2 g, 50 mmol). The mixture was stirred at 25° C. for one hour then refluxed for 5 hours. After cooling to 25° C., the mixture was poured onto ethyl acetate (200 mL) and washed with 1 M HCl (3×50 mL), then saturated aqueous NaCl (1×50 mL) and then dried over sodium sulfate. The solvent was removed and the crude acid azeotroped once with toluene.

Step 3—The crude material from step 2 was dissolved in 100 mL toluene, and 10 mL (1.63 g, 14 mmol) thionyl chloride was added and the resulting mixture was refluxed fro 90 minutes. The volume of the solution was reduced to approximately 30 mL by distillation, then the remaining toluene was removed by evaporation. The crude acid chloride was dissolved in 20 mL dry DCM and cooled to −70° C. under argon and a solution of approximately 10 mmol diazomethane in 50 mL anhydrous ether was added. The mixture was warmed to room temperature and stirred for 90 minutes. Argon was bubbled throught the solution for 10 minutes, then the solvents were removed by evaporation and the crude material was purified by flash chromatography, eluting with 10–20% ethyl acetate in hexane. The diazoketone (0.85 g, 1.4 mmol, 82% yield over three steps) was obtained as a pale yellow solid.

An improvement was made to the final diazomethylation step, whereby the acid chloride was reacted with (trimethylsilyl)-diaxomethane and triethylamine to give the identifier, which was then used without further purification. This was a significant improvement over the original reaction with diazomethane, as the identifier was now obtained in high yield with no chloromethylketone by-product. Also, purification by flash chromatography was no longer necessary, which in some cases had resulted in significant acid-catalyzed decomposition of the identifier.

ALTERNATE Step 3—5.7 mL (11.4 mmol, 3.00 eq.) of a 2.0 M solution of (trimethylsilyl)-diazomethane in hexanes was added to a solution of the acyl chloride (3.8 mmol, 1.00 eq.) and 1.85 mL (13.3 mmol, 3.5 eq.) of triethylamine in anhydrous THF/acetonitrile (1:1) at 0° C. under argon. The resulting orange solution was stirred at 0° C. for 2 hours, then at 25° C. for 17 hours. (If a precipitate immediately formed upon addition of the (trimethylsilyl)-dizomethane, DCM was added until the precipitate redissolved.) 250 mL of EtOAc was added and the organic layer was washed with 100 mL each of saturated aqueous $NaHCO_3$ and water, then dried with anhydrous $MgSO_4$. Removal of the volatiles in vacuo produced a yellow crystalline product at 60–100% yield.

In the synthesis of Example 1, ten identifiers were used to encode the combinatorial library. Step 1 used three pentachlorophenyl identifiers, those wherein n is 10–12 ($C_{10}Cl_5$, $C_{11}Cl_5$ and $C_{12}Cl_5$) and were encoded with the following binary encoding scheme: n is 10=100; n is 11=010; and n is 12=001. Step2 used two pentachlorophenyl identifiers, those wherein n is 8–9 ($C_8Cl_5$ and $C_9Cl_5$) and were encoded as: n is 8=10 and n is 9=01. Step 3 used five pentachlorophenyl identifiers, those wherein n is 3–7 ($C_3Cl_5$, $C_4Cl_5$, $C_5Cl_5$, $C_6Cl_5$ and $C_7Cl_5$) and were encoded as: n is 3=10000; n is 4=01000; n is 5=00100; n is 6=00010; and n is 7=00001.

Thus, in step 1, reagent 3 of Table 2-1 is encoded "011" which represents tagging this choice in the synthesis with two pentachlorophenyl identifiers, one wherein n is 11 and one wherein n is 12. Likewise, in step 3, reagent 14 of Table 2-3 is encoded "01110" which represents tagging this choice in the synthesis with three pentachlorophenyl identifiers, one wherein n is 4, one wherein n is 5 and one wherein n is 6.

In the synthesis of Example 2, eleven identifiers were used to encode the combinatorial library. Step 1 used three pentachlorophenyl identifiers, those wherein n is 10–12 ($C_{10}Cl_5$, $C_{11}Cl_5$ and $C_{12}Cl_5$) and were encoded as: n is 10=100; n is 11=010; and n is 12=001. Step 2 used two pentachlorophenyl identifiers, those wherein n is 8–9 ($C_8Cl_5$ and $C_9Cl_5$) and were encoded as: n is 8=10 and n is 9=01. Step 3' used two pentachlorophenyl identifiers, those wherein n is 6–7 ($C_6Cl_5$ and $C_7Cl_5$) and were encoded as: n is 6=01 and n is 7=10. Finally, step 4 used three pentachlorophenyl identifiers, those werein n is 3–5 ($C_3Cl_5$, $C_4Cl_5$ and $C_5Cl_5$) and were encoded as: n is 3=0100; n is 4=0010; and n is 5=0001. Also used in step 4 was one trichlorophenyl identifier wherein n is 6 ($C_6Cl_3$) and which was encoded as 1000.

Thus, in step 1, reagent 3 of Table 2-1 is encoded "011" which represents tagging this choice in the synthesis with two pentachlorophenyl identifiers, one wherein n is 11 and one wherein n is 12. Similarly, in step 3', reagent 2 of Table 3-1 is encoded "01" which represents tagging this choice in the synthesis with one pentachlorophenyl identifier, wherein n is 6.

EXAMPLE 1

13020 COMPOUND LIBRARY

Step 1—Sequential Attachment of Bis-Boc Lysine, Photo-labile Linker, $R^1$ Amines and Encoding 1a. Attachment of bis-Boc lysine to TentaGel™

TentaGel™ resin ($S-NH_2$, 10 g, 0.29 mmol/g, 2.9 mmol, 180–220 um) was suspended in a solution of bis-Boc lysine (8.7 mmol, 5.12 g) and HOBt (8.7 mmol, 1.18 g), then treated with DIC (17.4 mmol, 2.73 mL). The suspension was shaken overnight, then drained and washed with 150 mL each of DMF (3×), MeOH (3×) and DCM (3×). Resin 1 (Scheme 1) was then apportioned into seven reaction vessels, providing 2.14 g of resin 1 in each vessel.

1b. Encoding of resin 1

In each of the encoding steps, when the $C_nCl_5$-linker-diazoketone reagents (n is 3–12) were utilized, an amount of reagent equal to 7.5% by mass of the resin to be encoded was used. For the $C_5Cl_3$-linker-diazoketone reagents, an amount of reagent equal to 15% by mass of the resin to be encoded was used.

Prior to the addition of the photo-labile linker and the first combinatorial step, each of the seven resin batches of Step 1a were encoded with one or more of the $C_{10}Cl_5$-, $C_{11}Cl_5$- and $C_{12}Cl_5$-linker-diazoketones to produce the appropriate binary code. Identifiers were incorporated one at a time until the required binary code was completed. For example, 2.14 g of resin batch 3 was suspended in 50 mL of ethyl acetate and a solution of 0.16 g of $C_{12}Cl_5$-linker-diazoketone dissolved in 1.3 mL DCM was added. After the mixture was agitated for 2 hours, 2.6 mL of a 1/5 mg/mL solution of rhodium trifluoroacetate dimer in DCM was added and the resin agitated at 25° C. for a further 16 hours. The resin mixture was then filtered and washed with 50 mL each of DCM (4×), methanol (2×), DCM (4×) and ethyl acetate (1×). This resin batch was again suspended in 50 mL of ethyl acetate and then a solution of 0.16 g of $C_{11}Cl_5$-linker diazoketone dissolved in 1.3 mL DCM was added. After agitating this batch for 2 hours, 2.6 mL of a 1.5 mg/mL solution of rhodium trifluoroacetate dimer in DCM was added and the batch was agitated at 25° C. for a further 16 hours. The resin was then filtered and washed with 50 mL each of DCM (4×), methanol (2×) and DCM (4×), then dried in vacuo.

1c. Removal of Boc protecting group and attachment of photo-labile linker

A suspension of tagged resin 1 (2.14 g) in 1:1 TFA/DCM was shaken for 1 hour, then washed with 50 mL each DCM (3×), MeOH (3×), 4:1 MeOH-$Et_3N$ (1×), MeOH (3×), DMF (3×) and DCM (3×). This resin was then suspended in 25 mL DCM, then treated with 25 mL of a pre-incubated (45 min) solution of 4-bromomethyl-3-nitro benzoic acid (3.21 mmol, 0.83 g), HOBt (3.21 imnol, 0.43 g), DIC (6.42 mmol, 1.0 mL) in DCM. The suspension was shaken for 3 hours, then drained and washed with three 50 mL portions of DCM. This protocol was repeated in tandem for each of the seven tagged resin 1 batches.

1d. Addition of the $R^1$ amines 2.14 g of the step 1c resin was suspended in 50 mL THF and then treated with methylamine, compound 1 of Table 2-1 (10.7 mmol), then shaken overnight. The product was then drained and washed with 50 mL each DMF (3×), MeOH (3×), 10:1 MeOH/TFA (1×), MeOH (3×), DMF (3×) and DCM (3×). This procedure was carried out in tandem, for each of the 7 amnines in Table 2-1, then the resin was pooled, mixed, and divided into 3 batches.

Step 2—Addition of $R^2$ Statines and Encoding

2a. Attachment of the Boc $R^2$ statines 3.7 g of each of the three resin batches was independently suspended in 50 mL DMF and treated with one of the three Boc protected $R^2$ statines of Table 2-2 (4.78 mmol), DIEA (9.56 mmol, 1.66 mL), then HATU (4.78 mmol, 1.82 g). Each suspension was then shaken for 6 hours, then drained and washed with 50 mL each DMF (3×), MeOH (3×), DMF (3×) and DCM (3×).

2b. Encoding of step 2a resin

Each of the three resin batches prepared in step 2a was encoded with one or more of the $C_8Cl_5$- and $C_9Cl_5$-linker-diazoketones to produce the appropriate binary code. Identifiers were incorporated one at a time until the required binary code was completed. For example, 3.7 g of resin batch 1 was suspended in 85 mL ethyl acetate and a solution of 0.30 g of $C_9Cl_5$- linker-diazoketones dissolved in 2.5 mL DCM was added. After the mixture was agitated for 2 hours, 4.7 mL of a 1.5 mg/mL solution of rhodium trifluoroacetate dimer in DCM was added and the resin agitated at 25° C. for a further 16 hours. The resin was then filtered and washed with 90 mL portions of DCM (4×), methanol (2×) and DCM (4×), then dried in vacuo.

After encoding, the three batches were pooled as a suspension in DCM, mixed to homogeneity, filtered, then dried in vacuo. The dried resin 9 was then divided into two portions; one portion was taken to the next step of Example 1, and the remaining portion was set aside for the library prepared in Example 2.

Step 3—Encoding and Attachment of Fmoc-amino Acids

The first portion of resin 9 was apportioned into thirty-one reaction vessels, each containing 0.18 g of the resin 9. Encoding of these resin batches was done prior to deprotection and the third combinatorial step.

3a. Encoding

Each of the thirty-one resin batches was encoded with one or more of the $C_3Cl_5$-, $C_4Cl_5$-, $C_5Cl_5$-, $C_6Cl_5$- and $C_7Cl_5$-linker-diazoketones to produce the appropriate binary code. Identifiers were incorporated one at a time until the required binary code was completed. For example, 0.18 g of resin batch 1 was suspended in 5 mL ethyl acetate and a solution of 0.01 g of $C_7Cl_5$-linker-diazoketone dissolved in 0.1 mL DCM was added. After agitation of the mixture for 2 hours, 0.22 mL of a 1.5 mg/mL solution of rhodium trifluoroacetate dimer in DCM was added and the mixture was agitated at 25° C. for a further 16 hours. The resin was then filtered and washed with 5 mL portions of DCM (4×), methanol (2×) and DCM (4×), then dried in vacuo.

3b. Attachment of the Fmoc-amino acids

One of the Fmoc-amino acids (Table 2-3) was added to each of the thirty-one vessels containing a portion of tagged resin. For example, tagged resin batch 1, (0.17; 0.11 mmol g) was suspended in 8 mL of DMF containing Fmoc-alanine (0.16 mmol) and HATU (0.16 mmol). The suspension was shaken at room temperature for 10 minutes and then 0.33 mmol DIEA was added. The resulting mixture was shaken for 2 hours, during which time the resin in the vessel was continuously monitored with the Kaiser test to determine the level of amine functionality remaining. Once the coupling was complete (Kaiser test negative), the resin mixture was filtered and washed with 10 mL portions of DMF (3×), MeOH (3×) and DCM (3×). This procedure was repeated for each of the Fmoc-protected amino acids in Table 2-3. The resulting resin batches were then pooled and mixed.

Step 4—Fmoc-deprotection

The combined resin from step 3b (5.6 g) was suspended in 15 mL 30% piperidine in DMF and shaken for 1 hour at room temperature. The product was filtered, washed with 15 mL each DMF (2×), DCM (3×), MeOH (3×) and DCM (5×) and then dried under vacuum.

Step 5—Attachment of $R^4$ acids and deprotection.

The resin from step 4 was evenly divided into twenty reaction vessels, providing 0.28 g resin in each vessel. Each batch of resin was reacted with one of the carboxylic acid reagents depicted in Table 2–4. For example, resin batch one was reacted with benzoic acid (0.3 mmol), HATU (0.36 mmol) and DIEA (0.88 mmol) in 7 mL DMF. The resulting resin suspension was shaken for approximately one hour at room temperature, at which time the Kaiser test was negative. The resin was filtered and washed with 10 mL each DMF (2×), MeOH (3×) and DCM (5×). The batch was then shaken with a solution of TFA/phenol/thiophenol, EDT and water (82:5:5:3:5) for 1.5 hours at room temperature. This step removed all of the protecting groups on the amino acid side chains and on the $R^4$ acids. Following this step, the batch was filtered and subjected to a wash cycle of consecutive 10 mL portions of TFA/water (1:1) (2×), DMF (2×), MeOH (4×), DMF (2×) and DCM (5×), then dried in vacuo. The resin batches in all but one of the twenty reaction vessels was treated with one of the carboxylic acid reagents depicted in Table 2–4, the exception being resin batch eleven. Here, the anhydride was heated and shaken at 45° C. in DMF for 8 hours. Each of the final resin batches was individually recovered and stored as a separate sub-library, thereby obviating the need for encoding.

Verification of Synthesis

Two members from the library of Example 1 were synthesized on the solid phase to serve as quality controls for the integrity of the reagents and reaction conditions used for the library synthesis. The compounds were cleaved from the resin via photoelution of the resin at 50° C. for 3 to 4 hours at 353 nm. The structures were confirmed by $^1H$ NMR and mass spectroscopy.

EXAMPLE 2

18900 MEMBER LIBRARY

This library of compounds was prepared using the second portion of the pooled, mixed resin product obtained in accordance with steps 1 through 2b of Example 1; thus, we begin here with step 3'.

Step 3'—Encoding, Deprotection and Attachment of Diamino Acids

3'a. Encoding 3.64 g of the resin product of step 2b of Example 1 was split into three portions of 1.2 g each. Each batch was encoded with one of more the $C_6Cl_5$- and $C_7Cl_5$-linker diazoketones to produce the appropriate binary code, prior to removal of the Boc protecting group and the third combinatorial step. The same encoding protocol was used as described in Example 1 hereinabove. After tagging, the dried resin was pooled and mixed to homogeneity.

3'b. Deprotection and attachment of diamino acids

A suspension of 1.2 g tagged resin in 40% TFA/DCM was shaken for 1 hour, then drained and washed with consecutive 50 mL portions of DCM, (3×), MeOH (3×), 10% $Et_3N$/MeOH (1×), MeOH (3×) and DMF (3×). A suspension of this resin in DMF (50 mL) was treated with one of the diamino acids of Table 3-1 (3.28 mmol), DIEA (6.60 mmol, 1.15 mL), then HATU (3.28 mmol, 1.25 g). The suspension was shaken for 6 hours, then drained and washed with 50 mL each DMF (3×), MeOH (3×), DMF (3×), then DCM (3×) and filtered. The resin was dried in vacuo. This procedure was carried out in tandem, for each of the three diamino acids.

Step 4—Encoding and attachment of $R^6$ acids and aldehydes

4a. Encoding

The step 3'b resins were pooled and divided into 15 batches, each of which was encoded according to the protocol of Example 1, using the diazoketone tags $C_3Cl_5$-, $C_4Cl_5$-, $C_5Cl_5$- and $C_6Cl_3$-, as appropriate for the fifteen $R^6$ acids and aldehydes depict in Table 3-2.

4b. Deprotection and attachment of a carboxyaldehyde

A suspension of resin batch one (0.728 g) in 40% TFA/DCM (10 mL) was shaken for 1 hour, drained and washed with consecutive 10 mL portions of DCM (3×), MeOH (3×), 10% $Et_3N$/MeOH (1×), MeOH (3×), and DMF (3×). This resin, suspended in 2% HOAc/DMF (10 mL), was treated with phenethyl aldehyde (8.8 mmol), followed by the addition of $NaBH_3CN$ (4.4 mmol, 0.28 g). The product was shaken overnight, then drained and washed with 10 mL portions of DMF (3×), MeOH (3×), DMF (3×) and DCM (3×). The resin was dried in vacuo. Step 4b was repeated for step 4a resin batches 3, 4, 5, 6, 7, 9, 10 and 13 (see Table 3-2).

4c. Deprotection and attachment of a carboxylic acid

A suspension of step 4a resin batch two (0.728 g) in 40% TFA/DCM (10 mL) was shaken for 1 hour, then filtered and washed with 10 mL portions of DCM (3×), MeOH (3×), 10% Et₃N/MeOH (1×), MeOH (3×) and DMF (3×). The product, suspended in DMF (10 mL) was treated with phenethylcarboxylic acid (0.66 mmol), followed by DIEA (1.32 mmol, 0.23 mL) and then HATU (0.66 mmol, 0.25 g). The resulting resin was shaken for 6 hours, then drained and washed with 10 mL portions of DMF (3×), MeOH (3×), DMF (3×) and DCM (3×). The resin was dried in vacuo. Step 4c was repeated for step 4a resin batches 8, 11, 12, 14, and 15 (see Table 3-2).

Following the attachement of all fifteen $R^6$ choices, the resins were pooled, mixed, and divided into 20 reaction vessels for use in Step 5.

Step 5—Deprotection and attachment of $R^7$

A suspension of resin batch two (0.40 g) in DCM (10 mL) was treated with HOAc (4.8 mmol, 0.27 mL), Pd(PPh₃)₄ (0.072 mmol, 83 mg), then Bu₃SnH (2.4 mmol, 0.64 mL). The suspension was shaken for 1 hour, then drained and washed with 10 mL portions of DCM (3×), pyridine (3×), DCM (3×) and DMF (3×). The product was suspended in DMF (10 mL) and then treated with 3,4-dichlorophenyl acetic acid (0.36 mmol), followed by DIEA (0.72 mmol, 0.13 mL) and HATU (0.36 mmol, 0.14 g). This suspension was shaken for 6 hours, then drained and washed with 10 mL portions of DMF (3×), MeOH (3×), then DMF (3×) and DCM (3×). Reaction vessels 3 through 20 were treated in similar fashion with the carboxylic acids of Table 3-3. For resin batch three, the corresponding amino acid was coupled as its Fmoc carbamate, and deprotected using standard piperidine deprotection conditions (30% piperidine/DMF, 30 minutes at room temperature) following acylation. For resin batch one, the carboxylation step was omitted and only the deprotection step was carried out. Each of the twenty final resin batches was individually recovered and then stored as a separate sub-library obviating the need for further encoding.

Verification of Synthesis

Two members from the library of Example 2 were synthesized on the solid phase to serve as quality controls for the integrity of the reagents and reaction conditions used for the library synthesis. The compounds were cleaved from the resin via photoelution from the resin at 50° C. for 3 to 4 hours at 353 nm and the structures were confirmed by 1H NMR and mass spectroscopy.

EXAMPLE 3

DECODING PROCEDURE

The following protocol is used to decode the library compounds, i.e., to detach the compounds from the solid supports (beads). A bead is placed in a 1.3 mm diameter pyrex capillary tube with 2 μL of acetonitrile. 2 μL of a 0.1 M aqueous solution of ceric ammonium nitrate and 3 μL hexane are added to the tube and the two-phase mixture is briefly centrifuged. The tube is sealed and left at 35° C. for 16 hours. The tube is then opened and a syringe is used to remove the organic layer, which is then mixed with 1 μL of N,O-bis(trimethylsilyl)aetamide. The silated tagged solution (1 μL) is analyzed by gas chromatography with electron capture (EC) detection.

The GC analysis is performed with a Hewlett Packard 5890 Plus gas chromatograph. On column injection into a 5 m, 0.32 mm retention gap, connected to a 25 m, 0.2 mm crosslinked 5% phenylmethyl silicone column is used. The temperature and pressure programs for the analysis are 200° to 320° C., 15° C./min, then 320° C. for 10 min and 20 to 40 psi at 2 psi/min, then 40 psi for 10 min. The EC detector is maintained at 400° C. and the auxiliary gas is set at 35 psi.

The identity of the library compound attached to the bead being decoded is ascertained based upon the reagents utilized in the synthesis of the compound. These reagents are readily determined from the binary codes associated, respectively, with each of the identifiers for such reagents, as characterized through the procedure described hereinabove. The binary codes for each of the identifiers assigned to the various reagents used in the foregoing examples are shown accompanying Tables.

EXAMPLE 4

PREPARATION OF CARBOXYLIC ACID (23)

Referring to Scheme 9, diamino acid intermediate 23 was prepared according to the following chemistry. A solution of trans-4-hydroxy-L-proline 24 (2.40 g; 18.3 mmol) in 61 mL of 1:1 dioxane/water was basified by the addition of $K_2CO_3$ (3.04 g; 22 mmol). The solution was then treated with allyl chloroformate (1.94 mL; 18.3 mmol) at 0° C., held at 0° C. for 2 hours, then warmed to room temperature and held for 15 minutes. The reaction mixture was acidified to pH 4 by the addition of 20% aqueous citric acid. Extraction with ethyl acetate and flash chromatography by 1:5 ethyl acetate/hexane provided 2.15 g of compound 25 (10 mmol; 54.5%; colorless oil).

Compound 25 (2.14 g; 9.94 mmol) was mixed with 50 mL THF and treated with $CH_2N_2$ in $Et_2O$ at room temperature, then quenched with acetic acid. The reaction mixture was concentrated and partitioned between ether and 5% $NaHCO_3$. The aqueous layer was extracted with ethyl acetate and the combined organic layer was dried over sodium sulfate, concentrated and chromatographed on silica gel, yielding 1.62 g of compound 26 (7.06 mmol; 71.1%; light yellow oil).

Compound 26 (15.10 g; 65.87 mmol) in 73 mL $CCl_4$ was treated with $PPh_3$ (19.01 g; 72.5 mmol) and $CBr_4$ (32.57 g; 98.2 mmol). The reaction mixture was refluxed for 20 minutes and the solution was then filtered and concentrated, producing a yellow oil which was then washed with hexane and chromatographed by 1:4 ethyl acetate/hexane, yielding 10.01 g compound 27 (34.3 mmol; 52.5%; yellow solid). Mass spectrum: m/z=292/294.

Compound 27 (10.01 g; 34.3 mmol) and $NaN_3$ (4.46 g, 68.6 mmol) in 69 mL DMF was stirred overnight at room temperature. The reaction mixture was partitioned between water and ethyl acetate, wherein the the aqueous layer was extracted with ethyl acetate (3×) and the combined organic layer was washed with brine and dried over sodium sulfate. The crude product was chromatographed by 1:5 ethyl acetate/hexane, yielding 8.32 g of compound 28 (34.3 mmol; 100%). Mass spectrum: m/z=255.

Compound 28 (7.40 g; 29.1 mmol) in toluene (58 mL) was treated with $PPh_3$ (7.63 g; 29.1 mmol) and held at room temperature for 10 minutes. The reaction solution was cooled to 0° C., and acetaldehyde (0.49 mL; 9.13 mmol) was added dropwise in two portions. The reaction mixture was stirred for 24 hours at 0° C., then evaporated and dissolved in 58 mL of MeOH. This solution was treated with $NaBH_3CN$ (1.83 g) and held at room temperature for 24 hours. The reaction was quenched with saturated aqueous $NH_4Cl$, then partitioned between 10% $NaHCO_3$ and ethyl acetate. The crude compound was chromatographed by 1:5 ethyl acetate/hexane, yielding 3.5g of compound 29 (13.6 mmol; 47%).

Compound 29 (3.50 g; 13.7 mmol) in 28 mL acetonitrile was treated with $Et_3N$ (2.86 mL; 20.6 mmol) and $(Boc)_2O$ (3.59 g; 16.4 mmol) at 0° C. The reaction mixture was held at 0° C. for 30 minutes, then warmed to room temperature and held for 2 hours. The reaction mixture was acidified with 20% aqueous citric acid to pH 4. The solution was extracted with EtOAc and concentrated to yield compound 30. The crude Boc protected compound 30, in 20 mL of dioxane/THF/water (1:1:1) was treated with LiOH (2.0 g; 83.5 mmol), then refluxed overnight. The reaction mixture was acidified and partitioned between water and EtOAc. The organic layer was dried and concentrated. The crude product was chromatographed by 1:3 EtOAc/hexane, yielding 2.05 g of compound 23 (59.9 mmol; 43.7%; colorless oil).

TABLE 1

Linker Groups

| | Linker Group (—L'—) | Cleavage reagent |
|---|---|---|
| 1. | 2-nitrobenzyl-B | light |
| 2. | 2-nitrobenzyloxycarbonyl-B | light |
| 3. | 1-(2-nitrophenyl)ethyl-B | light |
| 4. | RO-substituted aryl-B | Ce(NH$_4$)$_2$(NO$_3$)$_6$ |
| 5. | 2-bromoaryl-B | Li, Mg, or BuLi |
| 6. | aryloxy-B | H$_3$O$^+$ |
| 7. | (2-methoxy)benzyloxy-B | H$_3$O$^+$ |
| 8. | furyl-B | 1) O$_2$ or Br$_2$, MeOH  2) H$_3$O$^+$ |
| 9. | —CH=CH(CH$_2$)$_2$— | O$_3$, OsO$_4$/IO$_4^-$, or KMnO$_4$ |
| 10. | —CH=CHCH$_2$— | O$_3$, OsO$_4$/IO$_4^-$, or KMnO$_4$ |

TABLE 1-continued

Linker Groups

| | Linker Group (—L'—) | Cleavage reagent |
|---|---|---|
| 11. | —CH$_2$CH=CH— | O$_3$, OsO$_4$/IO$_4^-$, or KMnO$_4$ |
| 12. | —CH=CHCH$_2$B— | (Ph$_3$)PRhCl(H) |
| 13. | —S—CH$_2$—B— | Hg$^{+2}$ |
| 14. | CHX-CH$_2$-B (X substituted) | Zn or Mg |
| 15. | CH(OH)-CH$_2$-B | Oxidation, e.g., Pb(OAc)$_4$ or H$_5$IO$_6$ |

R = H or lower alkyl; B = O or NH; and
X = electron withdrawing group such as Br, Cl, and I.
⌇ = point of attachment to C(O)

TABLE 2-1

Amine Reagents (R$^1$) and Encoding Scheme

| | Amine reagent | Binary Code |
|---|---|---|
| 1. | MeNH$_2$ | 001 |
| 2. | butylamine (CH$_3$CH$_2$CH$_2$CH$_2$NH$_2$) | 010 |
| 3. | MeO(CH$_2$)$_3$NH$_2$ | 011 |
| 4. | phenylpropylamine (PhCH$_2$CH$_2$CH$_2$NH$_2$) | 100 |
| 5. | benzylamine (PhCH$_2$NH$_2$) | 101 |
| 6. | 3-(aminomethyl)pyridine | 110 |
| 7. | 2-(aminomethyl)pyridine | 111 |

TABLE 2-2
Statine Reagents (R²) and Encoding Scheme.
| | Statine Reagent | Binary Code |
|---|---|---|
| 1. | 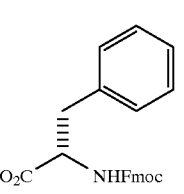 | 01 |
| 2. | | 10 |
| 3. | | 11 |
TABLE 2-3
Amino acid Reagents (Aa) and Encoding Scheme (Stereochemistry is as shown).
| | Aa Reagent | Binary Code |
|---|---|---|
| 1. | 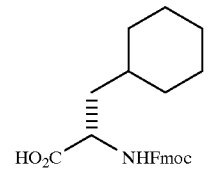 | 00001 |
| 2. | | 00010 |
| 3. | | 00011 |
| 4. | | 00100 |
| 5. | | 00101 |
TABLE 2-3-continued
Amino acid Reagents (Aa) and Encoding Scheme (Stereochemistry is as shown).
| | Aa Reagent | Binary Code |
|---|---|---|
| 6. | 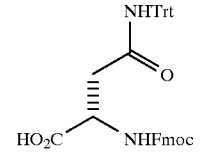 | 00110 |
| 7. | | 00111 |
| 8. | | 01000 |
| 9. | | 01000 |
| 10. | 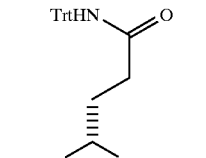 | 01010 |
| 11. | | 01011 |
| 12. | | 01100 |
| 13. | | 011101 |

TABLE 2-3-continued
Amino acid Reagents (Aa) and Encoding Scheme (Stereochemistry is as shown).
| Aa Reagent | Binary Code |
|---|---|
| 14. 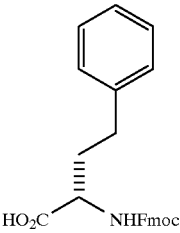 | 01110 |
| 15. 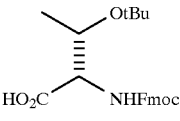 | 01111 |
| 16. 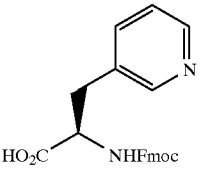 | 10000 |
| 17. 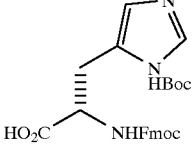 | 10001 |
| 18. 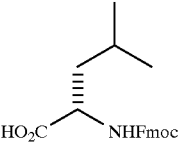 | 10010 |
| 19. 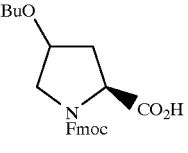 | 10011 |
| 20. 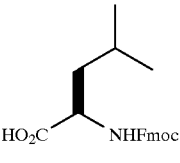 | 10100 |
| 21. 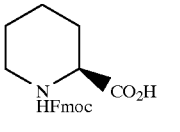 | 10101 |
| 22. 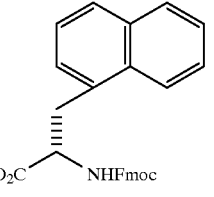 | 10110 |
| 23. 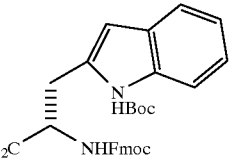 | 10111 |
| 24. 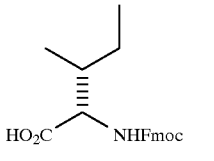 | 11000 |
| 25. 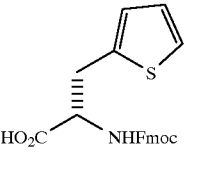 | 11001 |
| 26. 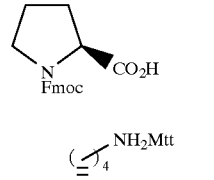 | 11010 |
| 27. 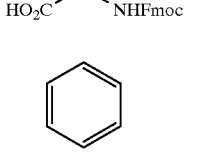 | 11011 |
| 28. 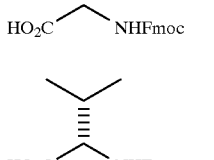 | 11100 |
| 29. 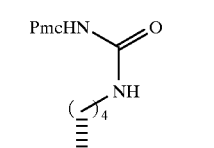 | 11101 |
| 30.  | 11110 |

TABLE 2-3-continued
Amino acid Reagents (Aa) and Encoding Scheme (Stereochemistry is as shown).
| | Aa Reagent | Binary Code |
|---|---|---|
| 31. | 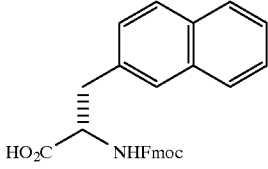 | 11111 |
TABLE 2-4
Carboxylic Acid Reagents (C(O)R$^4$)
| | Reagents |
|---|---|
| 1. | 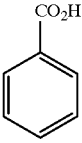 |
| 2. | 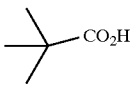 |
| 3. |  |
| 4. | 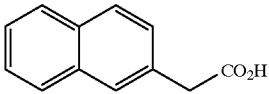 |
| 5. | 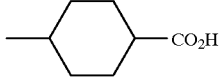 (racemic) |
| 6. | 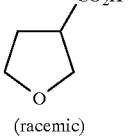 (racemic) |
| 7. | 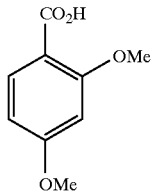 |
TABLE 2-4-continued
Carboxylic Acid Reagents (C(O)R$^4$)
| | Reagents |
|---|---|
| 8. | 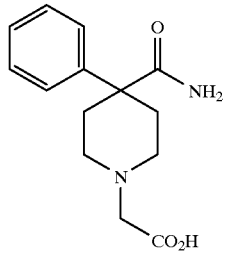 |
| 9. | 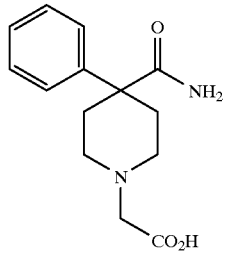 |
| 10. | 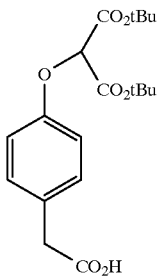 |
| 11. |  (racemic) |
| 12. | 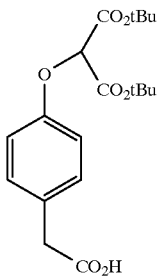 |
| 13. | 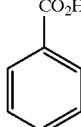 (racemic) |
| 14. | 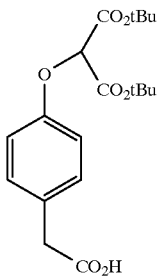 |
| 15. | 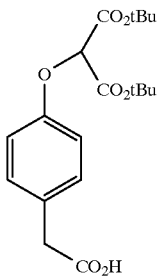 |

TABLE 2-4-continued

Carboxylic Acid Reagents (C(O)R⁴)

Reagents 16. 2,4-dichlorophenoxy propanoic acid structure (Cl, Cl on phenyl, O-CH2CH2-CO2H)

17. 5-phenyl-pyrrole with -CH2CH2-CO2H substituent 18. 4-(dimethylaminomethyl)benzoic acid (CO2H and CH2-NHMe2 on benzene)

19. 4-(pyrrolidinium-methyl)benzoic acid bromide (N+ pyrrolidine-CH2-C6H4-CO2H, Br⁻)

20. Phenylacetic acid (Ph-CH2-CO2H)

TABLE 3-1

Diamino acids (C(O)R⁵) and Encoding Scheme.

| | Diamine reagent | Binary Code |
|---|---|---|
| 1. | Piperazine with Boc on N4, Alloc on N1, CO2H at C2 (racemic) | 01 |
| 2. | Piperazine with Boc on N4, Alloc on N1, CH2-CO2H at C2 (racemic) | 10 |

TABLE 3-1-continued

Diamino acids (C(O)R⁵) and Encoding Scheme.

| | Diamine reagent | Binary Code |
|---|---|---|
| 3. | Pyrrolidine with N-Alloc, 2-CO2H, 4-N(Et)(Boc) (optically active) | 11 |

TABLE 3-2

Acid and Aldehyde Reagents (R⁶) and Encoding Scheme.

| | Reagent | Binary Code |
|---|---|---|
| 1. | 3-phenylpropanal (Ph-CH2CH2-CHO) | 0001 |
| 2. | 3-phenylpropanoic acid (Ph-CH2CH2-CO2H) | 0010 |
| 3. | 4-pyridinecarboxaldehyde | 0011 |
| 4. | 3,4,5-trimethoxybenzaldehyde | 0100 |
| 5. | 3-(3,4-dichlorophenoxy)benzaldehyde | 0101 |
| 6. | 3,4-dichlorobenzaldehyde | 0110 |

TABLE 3-2-continued

Acid and Aldehyde Reagents ($R^6$) and Encoding Scheme.

| Reagent | Binary Code |
|---|---|
| 7. 2-phenethoxyacetaldehyde | 0111 |
| 8. propionic acid | 1000 |
| 9. 4-biphenylcarboxaldehyde | 1001 |
| 10. 4-acetamidobenzaldehyde | 1010 |
| 11. 4-methylpentanoic acid | 1011 |
| 12. 3,5-bis(trifluoromethyl)phenylacetic acid | 1100 |
| 13. 3-pyridinecarboxaldehyde | 1101 |
| 14. methoxyacetic acid | 1110 |
| 15. adipic acid monoethyl ester | 1111 |

TABLE 3-3

Carboxylic Acid Reagents ($R^7$)
Carboxylic Acid Reagents

1. H
2. allyl hydrogen carbonate
3. 3-(4-chlorophenyl)-4-aminobutanoic acid (racemic)
4. methoxyacetic acid
5. methyl hydrogen succinate
6. ethyl hydrogen adipate
7. nicotinic acid
8. isonicotinic acid
9. 4-isopropoxybenzoic acid
10. 2-methoxybenzoic acid

TABLE 3-3-continued
Carboxylic Acid Reagents (R⁷)
Carboxylic Acid Reagents
11. – 20.
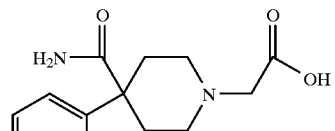
Scheme 1
Attachment of bis-Boc lysine to resin
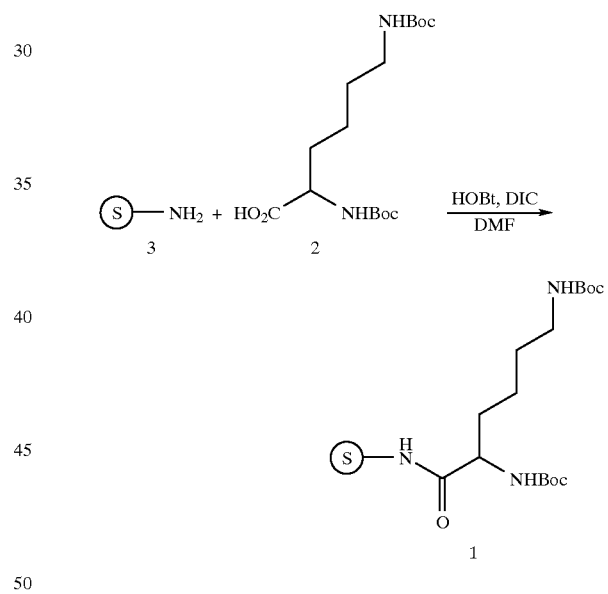
Scheme 2
Attachment of BNB linker and addition of amines (R¹)
1. BNB attachment
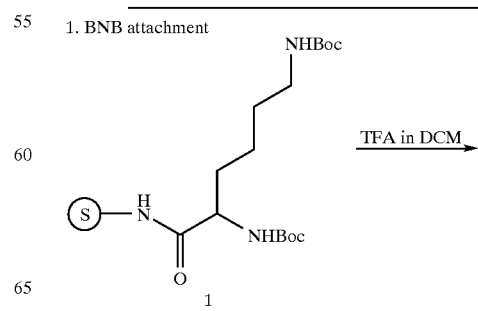

-continued
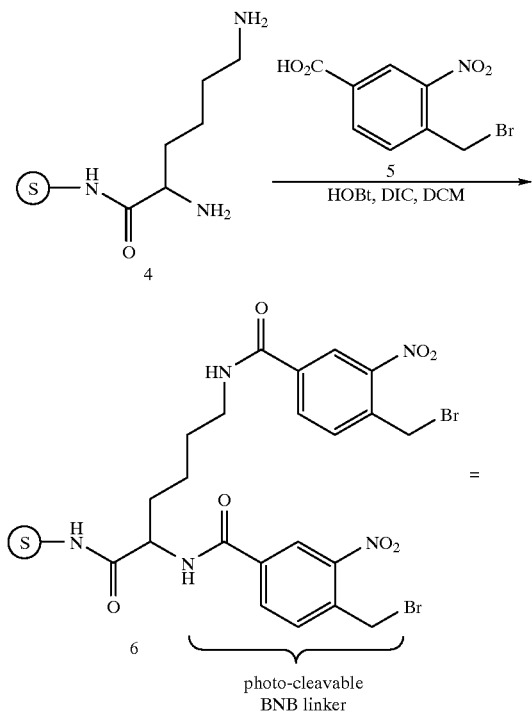
photo-cleavable BNB linker
2. Amine ($R^1$) attachment
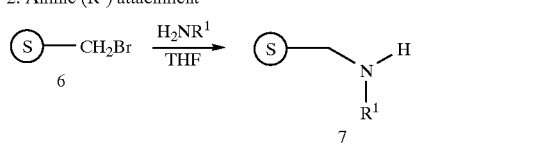
(See Table 2-1 for a selection of $R^1$ amines)
Scheme 3
Attachment of hydroxy-amino acids
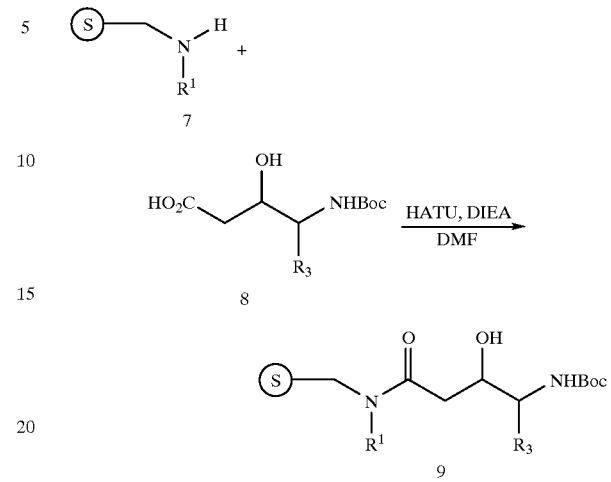
(See Table 2-2 for a selection of hydroxy-amino acid reagents)
Scheme 4
Removal of Boc protecting group and attachment of Fmoc-amino acids
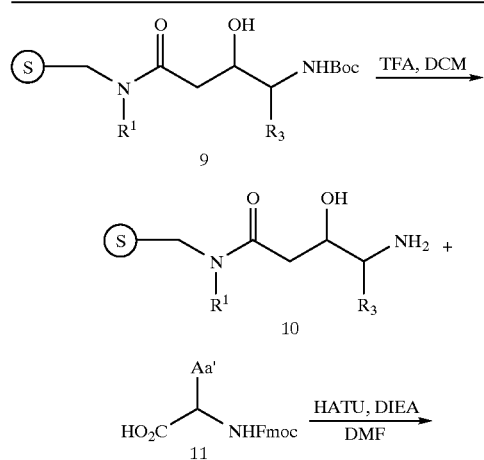

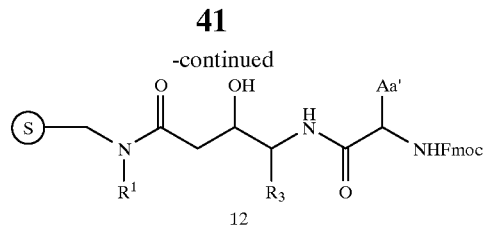

12

(Aa' refers to an amino acid side chain which may be protected by an acid labile protecting group; see Table 2-3 for a selection of Fmoc-amino acids)

Scheme 5
Removal of Fmoc protecting group, attachment of N-terminal $R^4$ groups and amino acid side chain deprotection

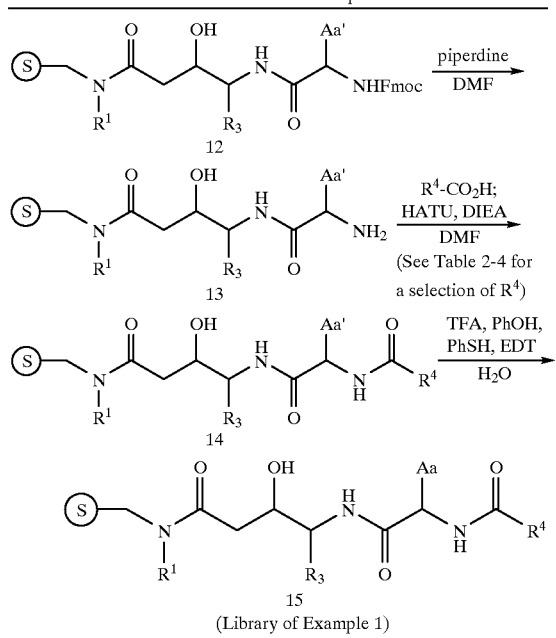

15
(Library of Example 1)

(Aa refers to an amino acid side chain in which an acid-labile side chain-protecting group is removed)

Scheme 6
Removal of Boc protecting group and attachment of diamino acids

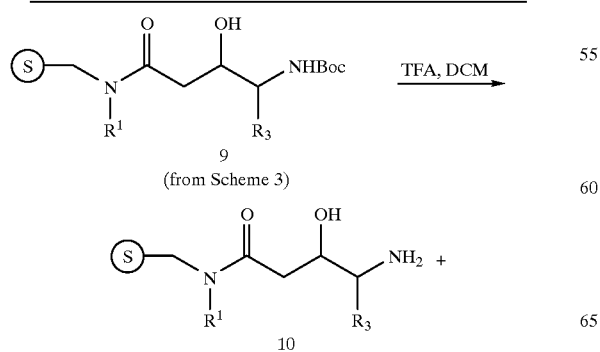

-continued

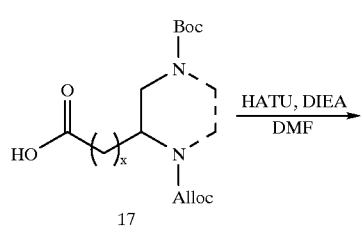

17

-continued
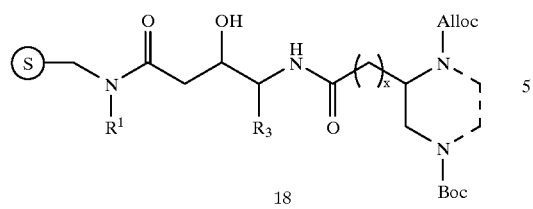
(See Table 3-1 for a selection of diamino acids)
Scheme 7
Removal of the Boc protecting group and acylation or reductive amination of secondary amine
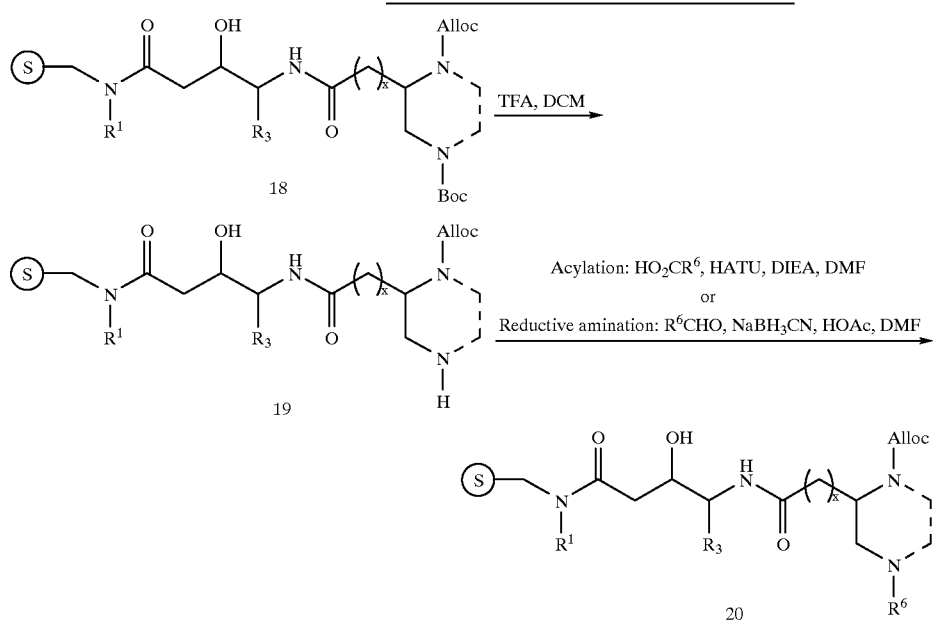
(See Table 3-2 for a selection of $R^6$)
Scheme 8
Removal of the Alloc protecting group and acylation of secondary amine
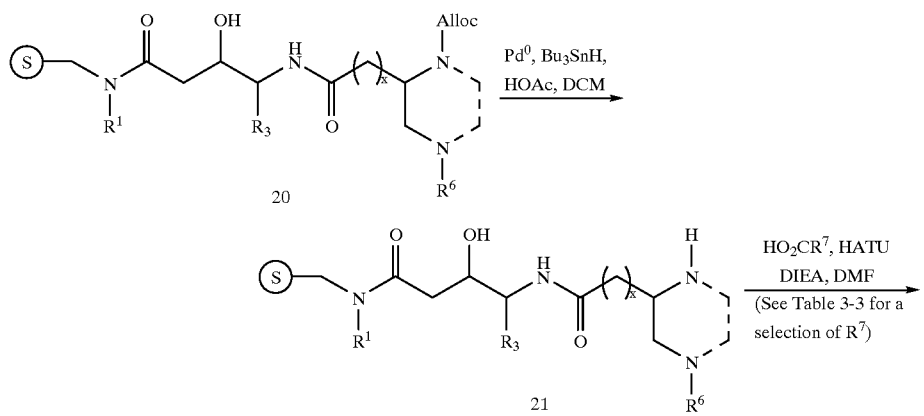

(Library of Example 2)
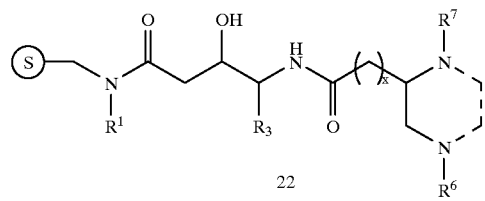
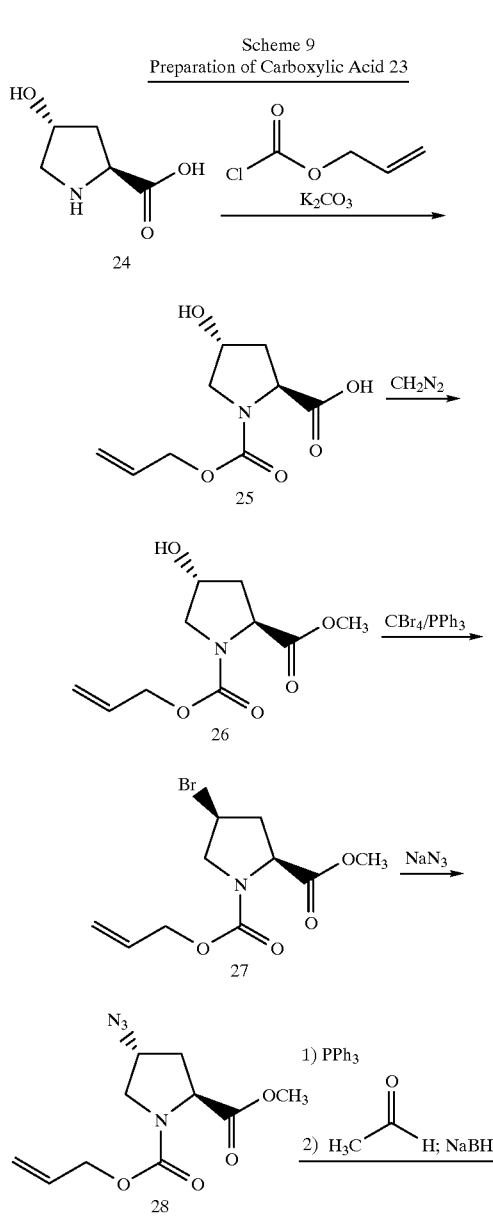
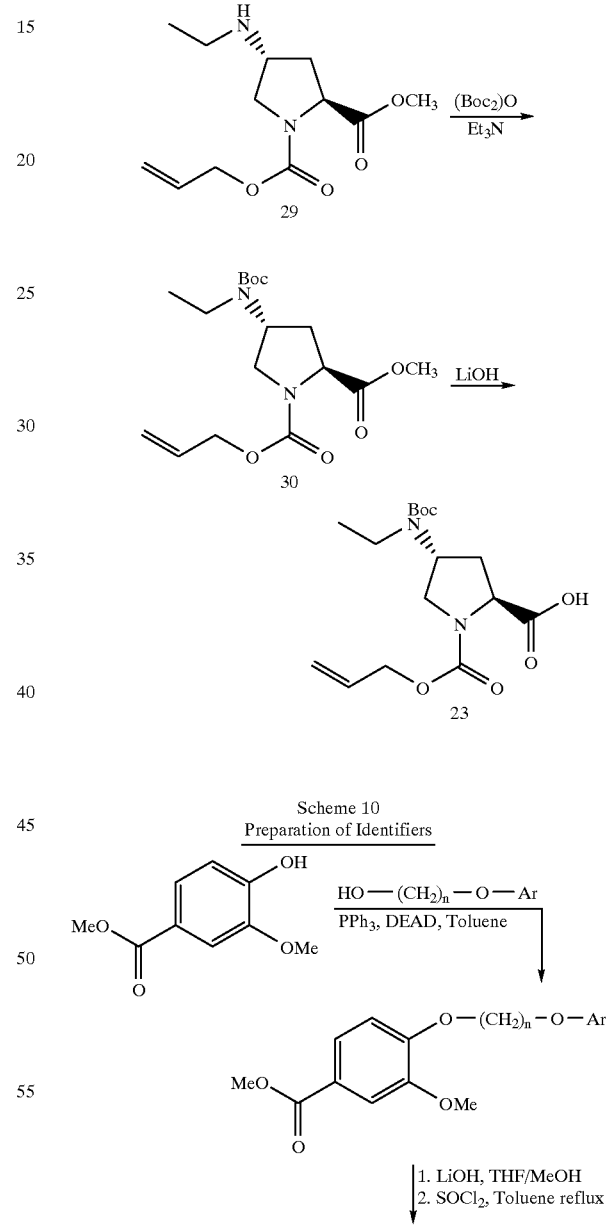

-continued

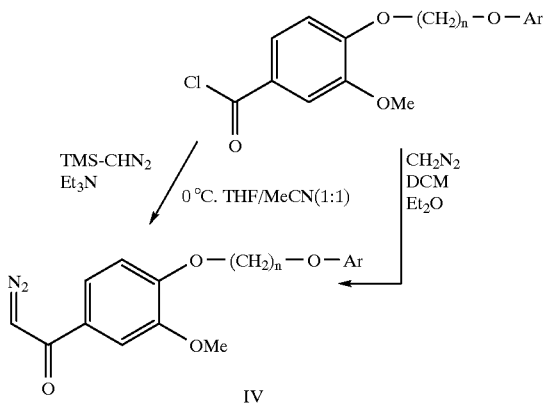

IV

We claim:

1. A combinatorial chemical library comprising a plurality of members of Formula I $$(T-L-)_q \text{S}-C(O)-L'-Z \qquad I$$

wherein:

Ⓢ is a solid support;

T—L— is an identifier residue;

—L'—Z is a linker/compound residue;

q is 0–30; and

—Z is

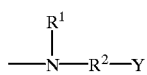

wherein:

R$^1$ is chosen from the group consisting of H, alkyl, cycloalkyl and substituted alkyl; and R$^2$ is —C(O)CH$_2$CH(OH)CH(R$^3$)NH— wherein:

R$^3$ is chosen from the group consisting of H, alkyl, aryl, arylalkyl and heteroarylalkyl; and Y is —C(O)R$^4$, —AaC(O)R$^4$, or —C(O)R$^5$;

wherein:

R$^4$ is chosen from the group consisting of alkyl, aryl, heteroaryl, mono substituted alkyl, cycloalkyl, substituted cycloalkyl, heterocycloalkyl and substituted heterocycloalkyl;

Aa is an amino acid;

R$^5$ is

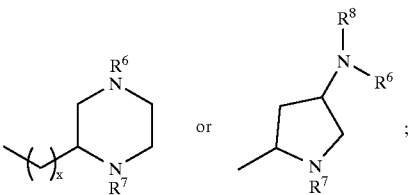

wherein:

x is 0 or 1;

R$^6$ and R$^7$ are independently chosen from the group consisting of H, alkyl, substituted alkyl, alkylcarbonyl, substituted alkylcarbonyl and C(O)R$^4$; and R$^8$ is alkyl or arylalkyl.

2. The combinatorial chemical library of claim 1, wherein q is zero, of Formula I'

$$\text{Ⓢ}—C(O)—L'—Z \qquad I$$

3. The combinatorial chemical library of claim 1 wherein q is 1–30 and T—L— is of Formula II

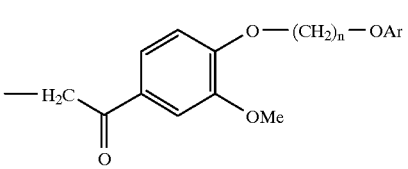

wherein:

n is 3–12; and

Ar is halophenyl; and q is 3–12.

4. The combinatorial chemical library of claim 3 wherein
1) n is 3–12 and Ar is a pentachlorophenyl; or
2) n is 3–6 and Ar is 2,4,6-trichlorophenyl.

5. The combinatorial chemical library of claim 1 wherein —L'— is of Formula (a)

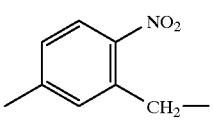

wherein the left-hand bond is the point of attachment to —C(O)— and the right-hand bond is the point of attachment to —Z.

6. The combinatorial chemical library of claim 1 wherein $R^1$ is chosen from the group consisting of methyl, butyl, 3-methyoxypropyl, 3-phenylpropyl, benzyl, (3-pyridinyl)methyl and (2-pyridinyl)methyl.
$R^2$ is
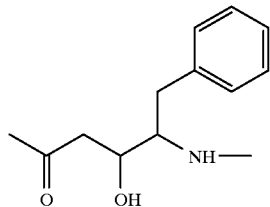
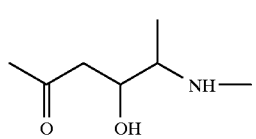
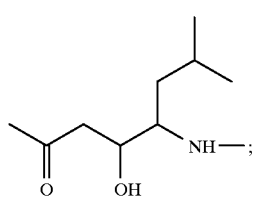
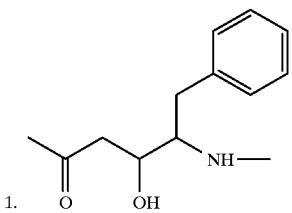
1.
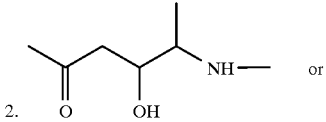
2.      or
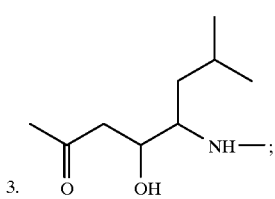
3.
wherein the left-hand bond is the point of attachment to $N(R^1)$; and the right-hand bond is the point of attachment to Y.
Y is —Aa—C(O)$R^4$;
Aa is
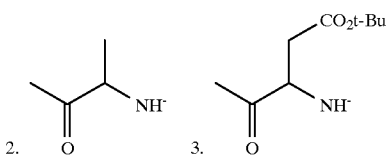
2.      3.
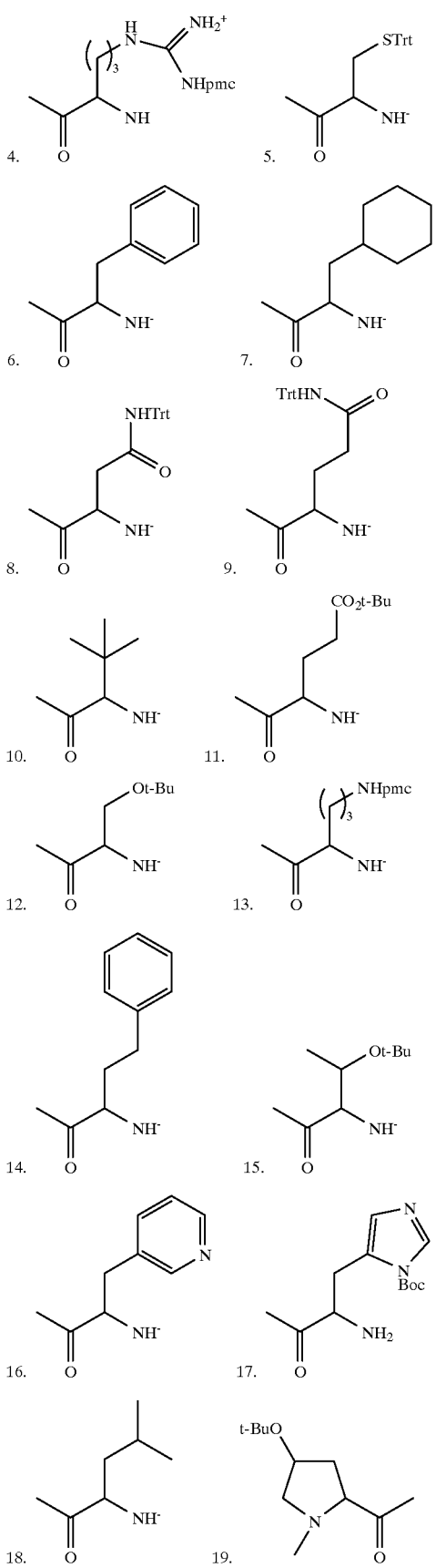

-continued
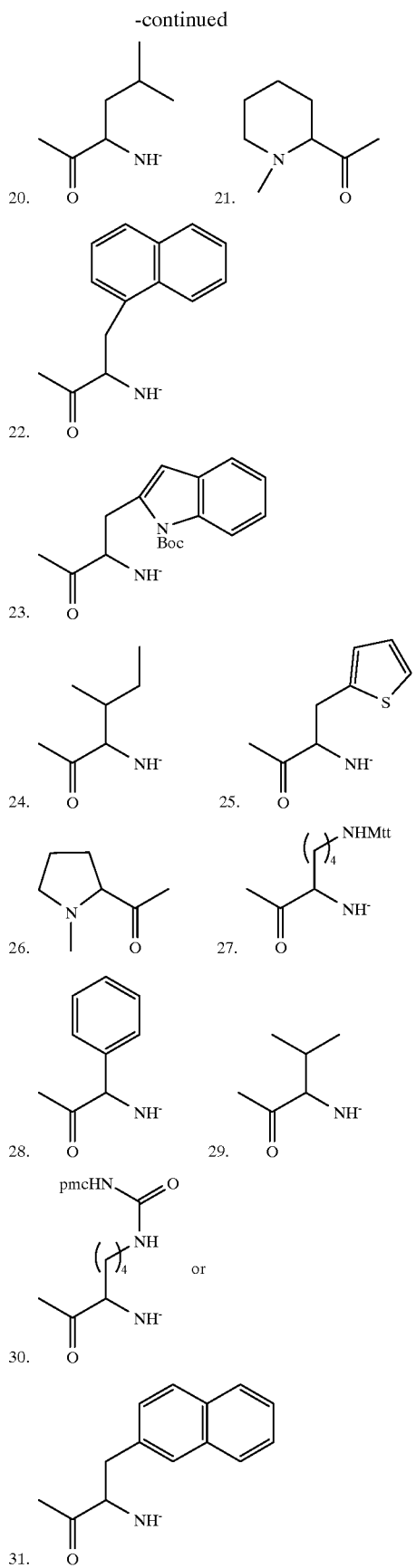
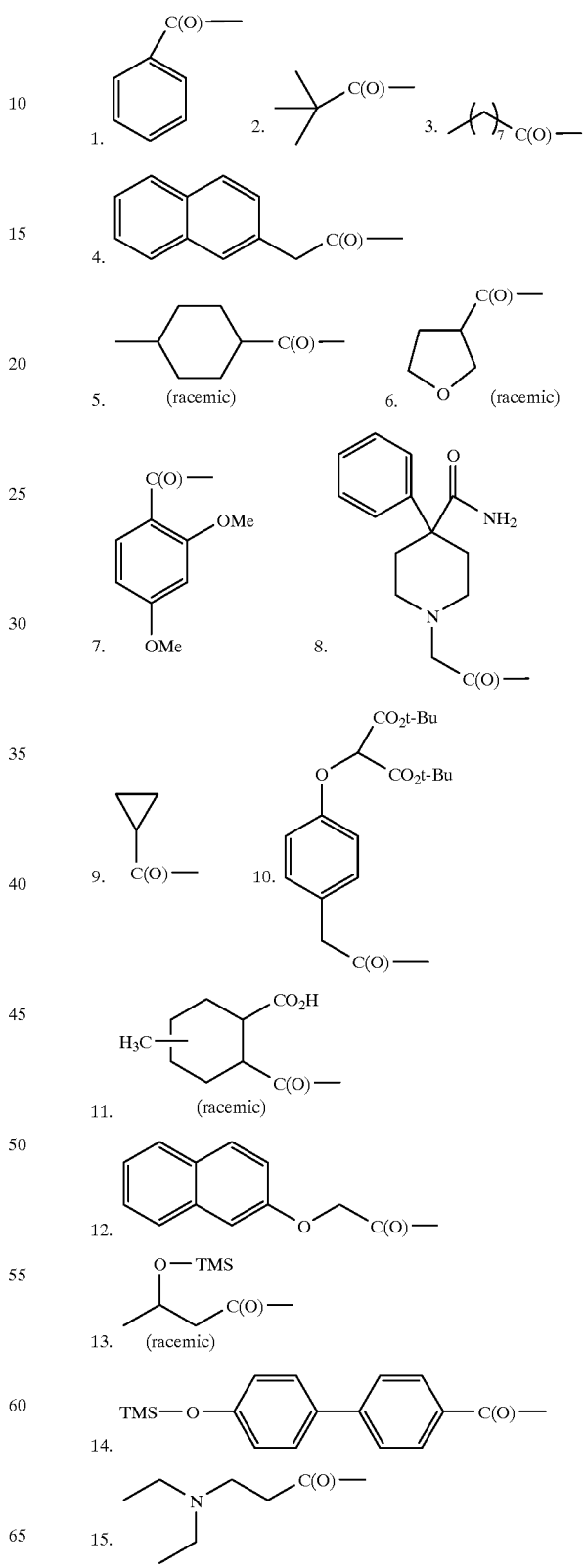
wherein the left-hand bond is the point of attachment to $R^2$ and the right-hand bond is the point of attachment to —C(O)$R^4$; and
$R^4$ is -continued
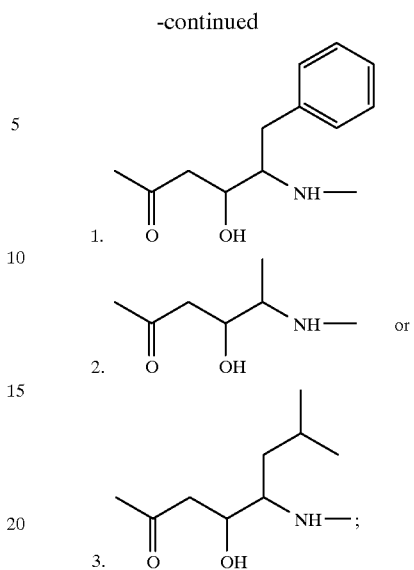
16.
17.
18.
19.
20.
7. The combinatorial chemical library of claim 1 wherein:
R¹ is chosen from the group consisting of methyl, butyl, 3-methoxypropyl, 3-phenylpropyl, benzyl, (3-pyridinyl)methyl and (2-pyridinyl)methyl.
R² is
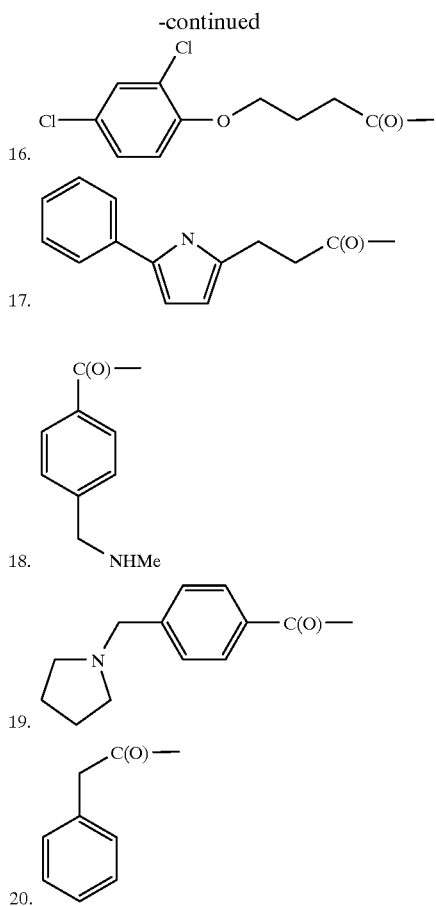
-continued
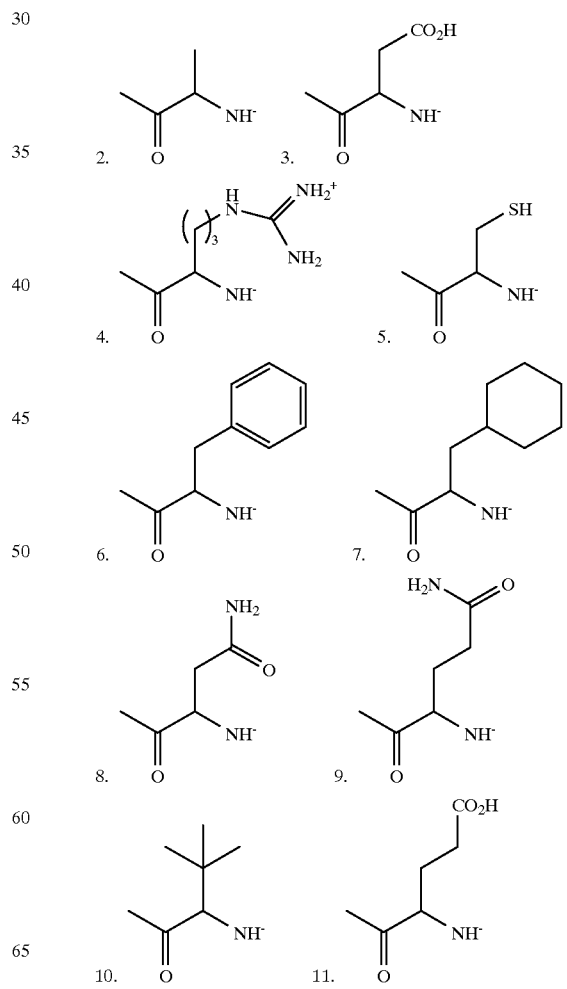
1.
2. or
3.
wherein the left-hand bond is the point of attachment to N(R¹); and the right-hand bond is the point of attachment to Y;
Y is —Aa—C(O)R⁴;
Aa is
2. 3.
4. 5.
6. 7.
8. 9.
10. 11.
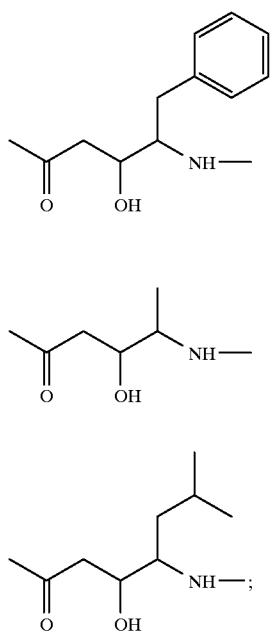

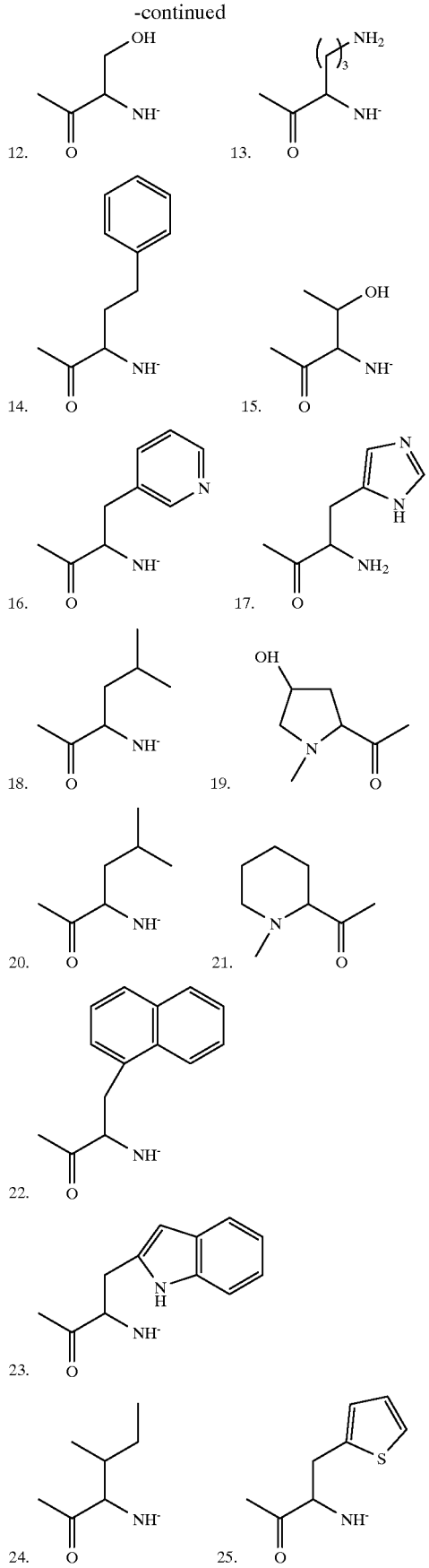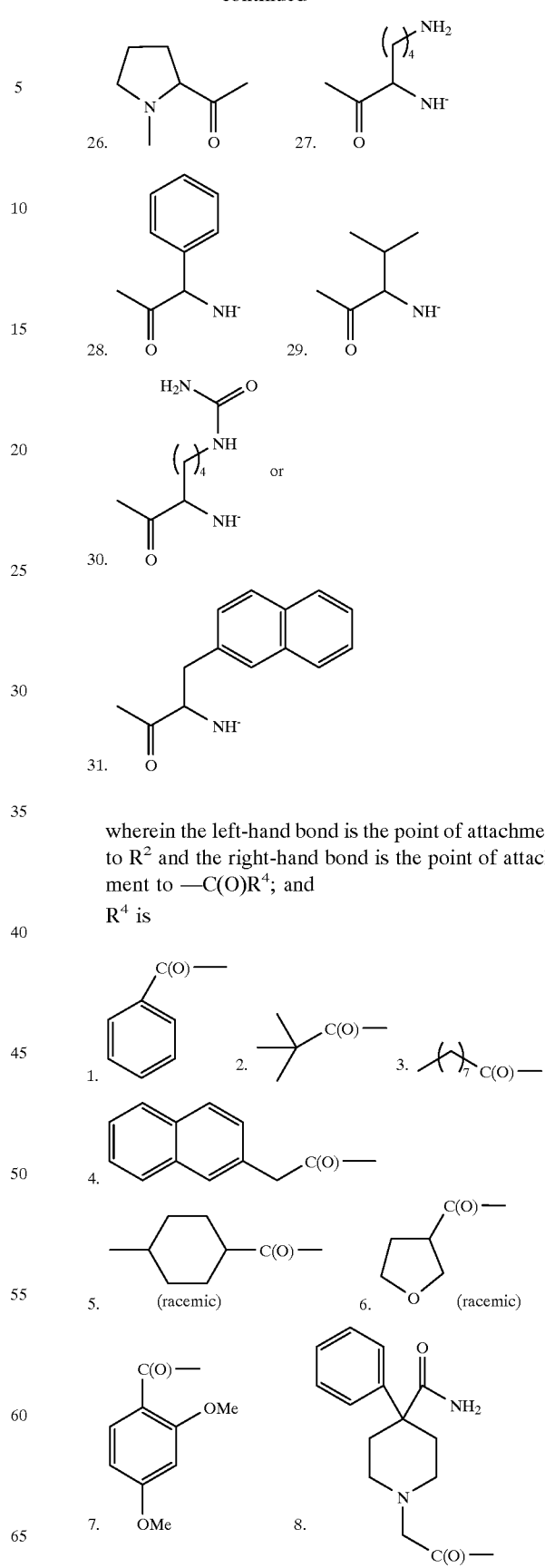
wherein the left-hand bond is the point of attachment to $R^2$ and the right-hand bond is the point of attachment to —C(O)R$^4$; and
R$^4$ is 9. 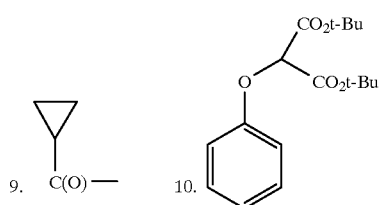
10.
11. (racemic) 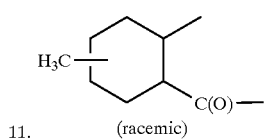
12. 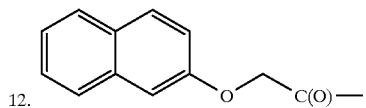
13. (racemic) 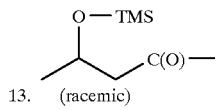
14. 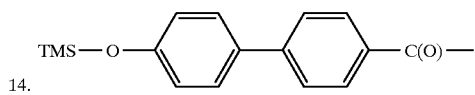
15. 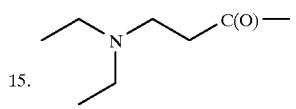
16. 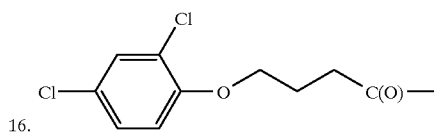
17. 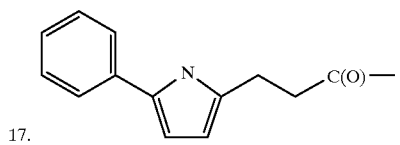
18. 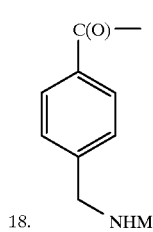
19. 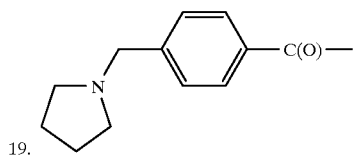
20. 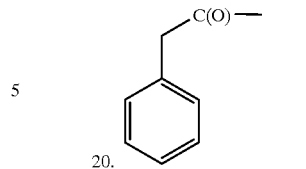
8. The combinatorial chemical library of claim 1 wherein:
R$^1$ is chosen from the group consisting of methyl, butyl, 3-methyoxypropyl, 3-phenylpropyl, benzyl, (3-pyridinyl)methyl and (2-pyridinyl)methyl.
R$^2$ is
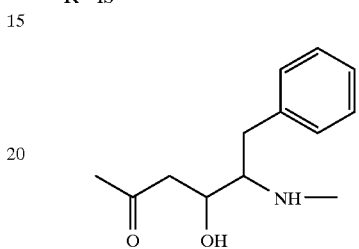
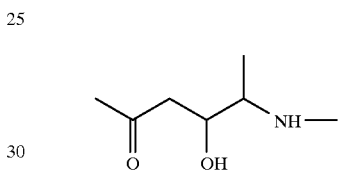
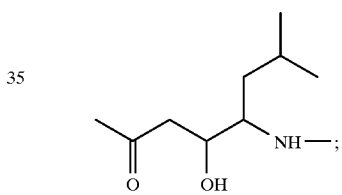
1. 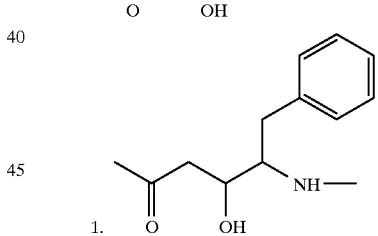
2. 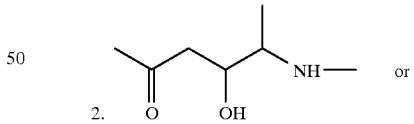 or
3. 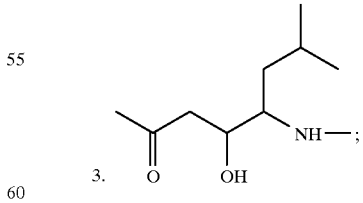
wherein the left-hand bond is the point of attachment to N(R$^1$); and the right-hand bond is the point of attachment to Y;
Y is —C(O)R$^5$;

$R^5$ is
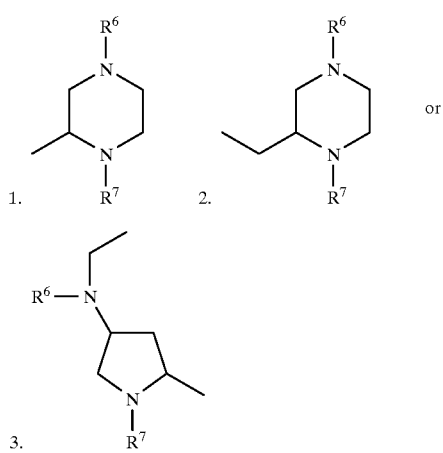
$R^6$ is
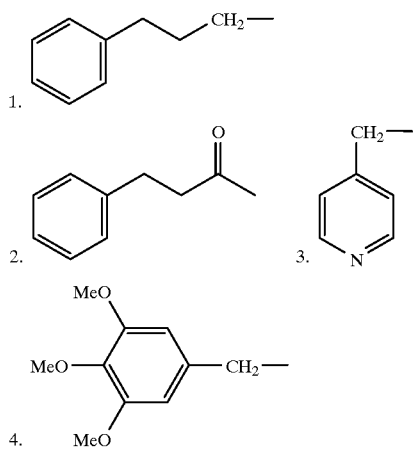
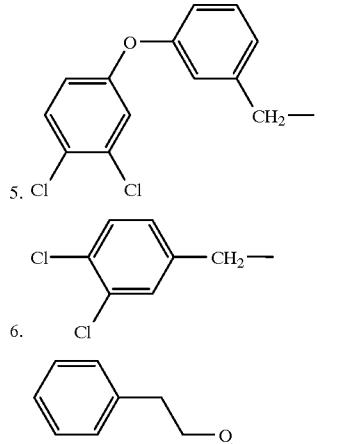
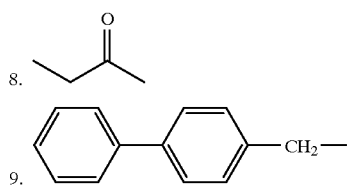
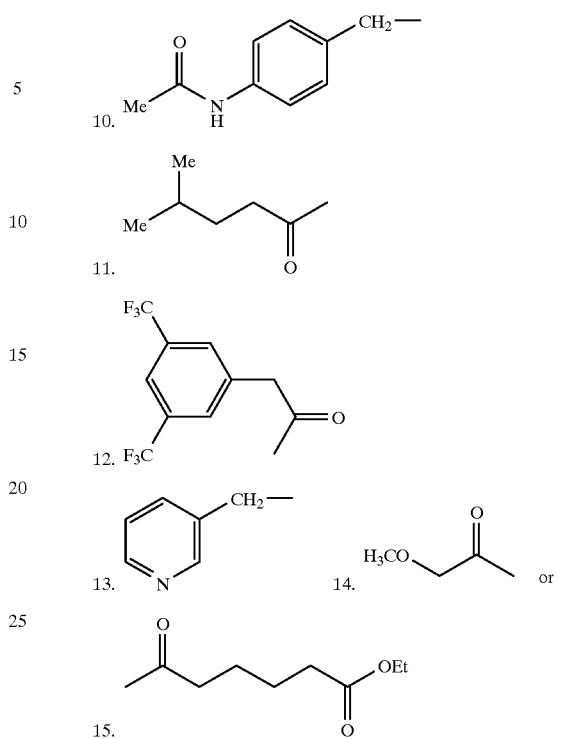
$R^7$ is
1. H

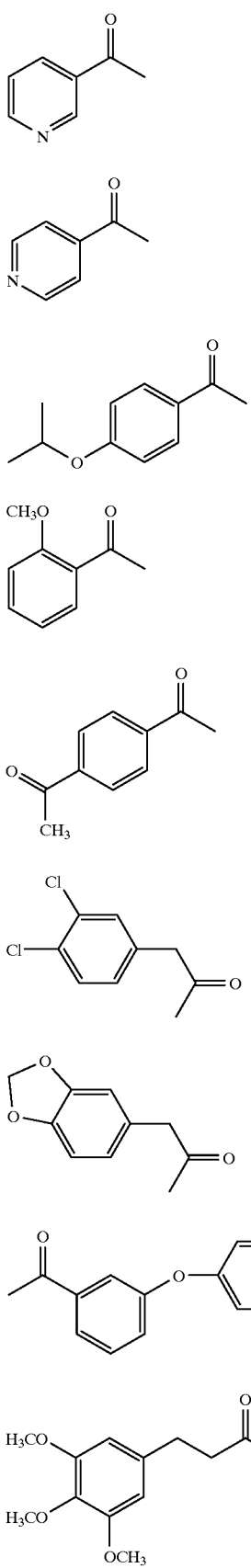
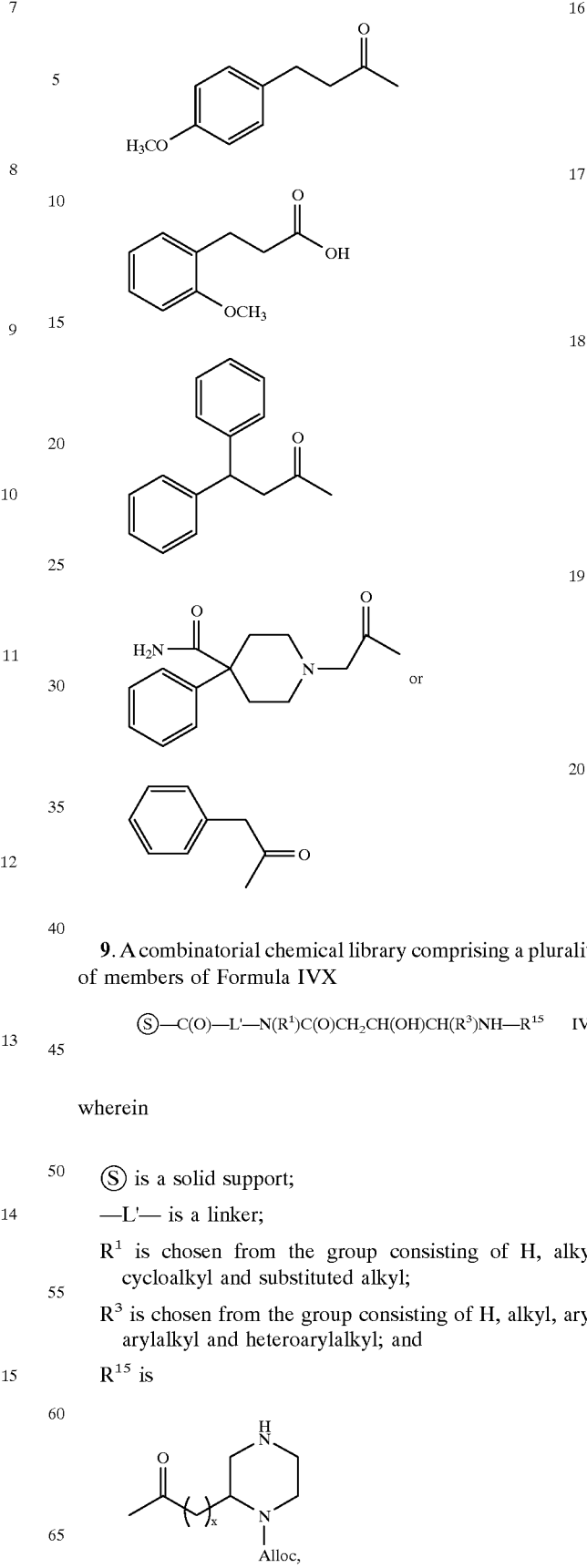

9. A combinatorial chemical library comprising a plurality of members of Formula IVX $$\text{(S)}-C(O)-L'-N(R^1)C(O)CH_2CH(OH)CH(R^3)NH-R^{15} \quad \text{IVX}$$

wherein (S) is a solid support;

—L'— is a linker;

$R^1$ is chosen from the group consisting of H, alkyl, cycloalkyl and substituted alkyl;

$R^3$ is chosen from the group consisting of H, alkyl, aryl, arylalkyl and heteroarylalkyl; and $R^{15}$ is -continued
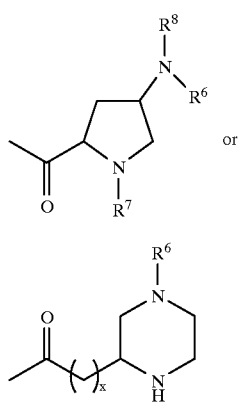
wherein
—Aa— is chosen from
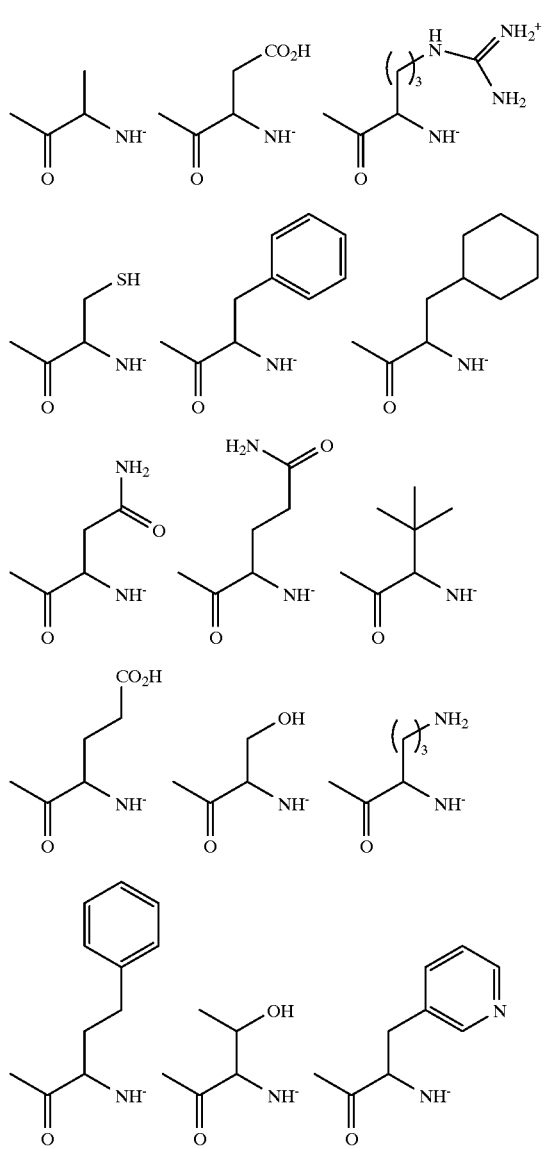
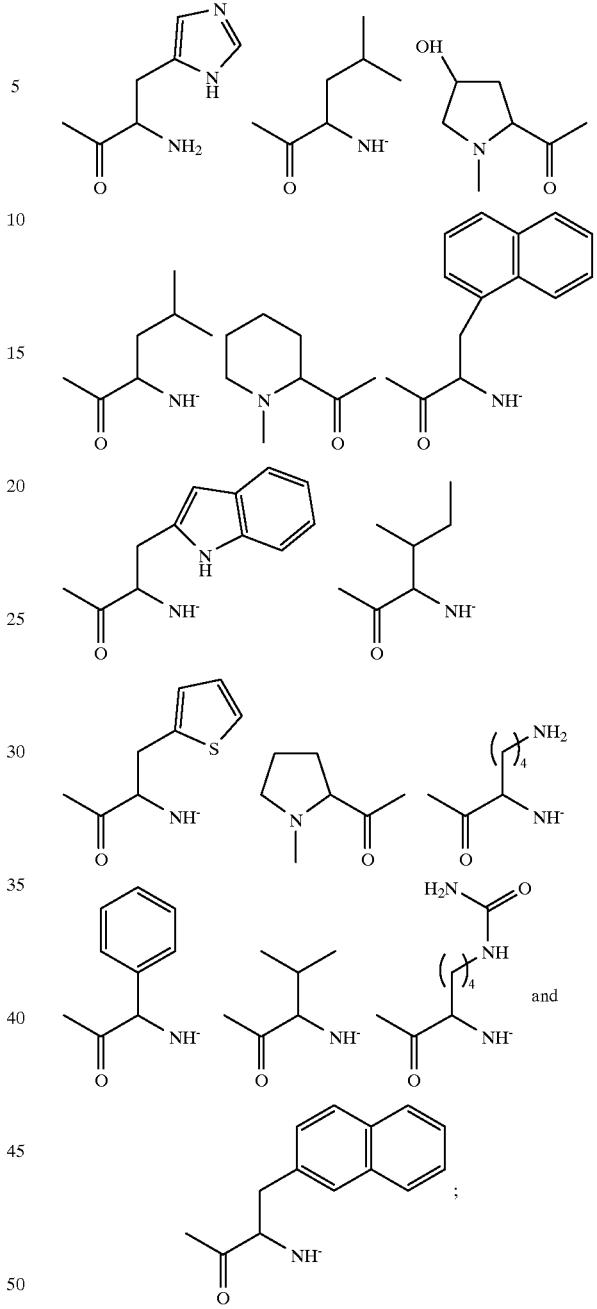
x is 0,1;
$R^6$ and $R^7$ are each independently H, alkyl, substituted alkyl, alkylcarbonyl or substituted alkylcarbonyl; and
$R^8$ is alkyl or arylalkyl.
10. The combinatorial chemical library of claim 9 of Formula IVa
$$(S)-C(O)L'N(R^1)C(O)CH_2CH(OH)CH(R^3)NH-Aa-H \qquad IVa.$$
11. The combinatorial chemical library of claim 9 of Formula IVb

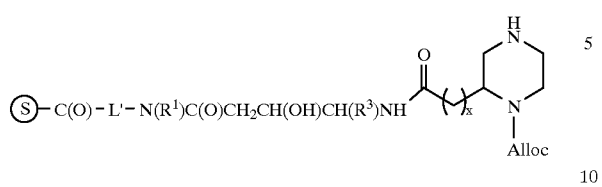
IVb
12. The combinatorial chemical library of claim 9 of Formula IVc
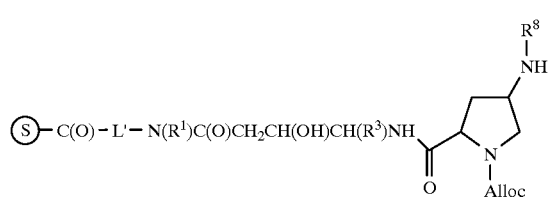
IVc
13. The combinatorial chemical library of claim 9 of Formula IVd
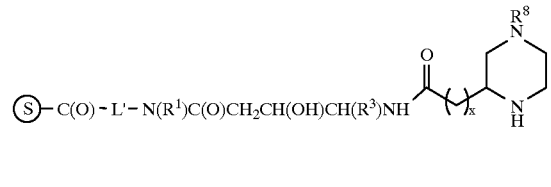
IVd
14. The combinatorial chemical library of claim 9 of Formula IVe
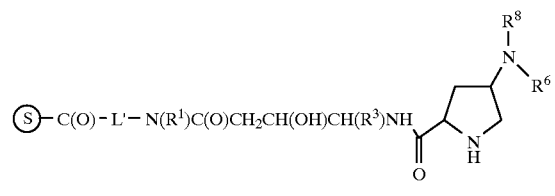
IVe
* * * * *

UNITED STATES PATENT AND TRADEMARK OFFICE
CERTIFICATE OF CORRECTION

PATENT NO. 5,972,719

DATED Oct. 26, 1999

INVENTOR(S) Dolle, III et al.

It is certified that error appears in the above-identified patent and that said Letters Patent is hereby corrected as shown below:

Col. 49, lines 35-50    delete structures numbered 1., 2., 3.

Col. 54, lines 5-20    delete structures numbered 1., 2., 3.

Col. 58, lines 45-60    delete structures numbered 1., 2., 3.

Col. 62, line 58    "$R^{15}$ is" should be --$R^{15}$ is --Aa-H--

Col. 66, line 5    "$R^8$" should be --$R^6$--

Signed and Sealed this

Second Day of January, 2001

Attest:

Attesting Officer

Q. TODD DICKINSON

Commissioner of Patents and Trademarks

UNITED STATES PATENT AND TRADEMARK OFFICE
CERTIFICATE OF CORRECTION

PATENT NO.    : 5,972,719
DATED         : October 26, 1999
INVENTOR(S)   : Dolle, III et al.

Page 1 of 1

It is certified that error appears in the above-identified patent and that said Letters Patent is hereby corrected as shown below:

Column 49,
Lines 6-30, delete the first three structures of substituent $R^2$

Column 53,
Lines 45-65, delete the first three structures of substituent $R^2$

Column 58,
Lines 15-40, delete the first three structures of substituent $R^2$

Column 62,
Line 58, "$R^{15}$ is" should be -- $R^{15}$ is -Aa-H, --

Column 66,
Line 5, "$R^8$" should be -- $R^6$ --

Signed and Sealed this

Thirteenth Day of May, 2003

JAMES E. ROGAN
*Director of the United States Patent and Trademark Office*